United States Patent
Choi et al.

(10) Patent No.: US 7,968,003 B2
(45) Date of Patent: Jun. 28, 2011

(54) PYRAN DERIVATIVE, ITS PREPARATION METHOD, LIQUID CRYSTAL COMPOSITION AND LIQUID CRYSTAL DISPLAY DEVICE COMPRISING THE SAME

(75) Inventors: Bum-Gyu Choi, Daejeon (KR); Min-Jin Ko, Daejeon (KR); Myung-Sun Moon, Daejeon (KR); Jae-Ho Cheong, Daejeon (KR); Dae-Ho Kang, Daejeon (KR); Ki-Youl Lee, Daejeon (KR); Yun-Bong Kim, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 12/585,247

(22) Filed: Sep. 9, 2009

(65) Prior Publication Data

US 2010/0059710 A1  Mar. 11, 2010

(30) Foreign Application Priority Data

Sep. 11, 2008 (KR) .................. 10-2008-0089931

(51) Int. Cl.
*C09K 19/00* (2006.01)
*C09K 19/30* (2006.01)
*C09K 19/32* (2006.01)
*C09K 19/34* (2006.01)
*C09K 19/52* (2006.01)

(52) U.S. Cl. ........... 252/299.6; 252/299.01; 252/299.61; 252/299.62; 252/299.63; 549/427; 549/428; 428/1.1; 430/20

(58) Field of Classification Search .................. 549/427, 549/428; 428/1.1; 252/299.01, 299.6, 299.61–299.63; 430/20
See application file for complete search history.

(56) References Cited

U.S. PATENT DOCUMENTS 7,314,943 B2 * 1/2008 Poetsch et al. ................ 549/428
* cited by examiner

*Primary Examiner* — Geraldina Visconti
(74) *Attorney, Agent, or Firm* — McKenna Long & Aldridge LLP

(57) ABSTRACT

The present invention relates to a pyran derivative which manifests appropriate refractive anisotropy (optical anisotropy) and liquid crystal transition temperature and excellent dielectric anisotropy, and has excellent compatibility with various liquid crystal compounds, and thus, can be preferably used for the formation of a liquid crystal layer of a liquid crystal display device, its preparation method, a liquid crystal composition and liquid crystal display device comprising the same.

20 Claims, No Drawings

PYRAN DERIVATIVE, ITS PREPARATION METHOD, LIQUID CRYSTAL COMPOSITION AND LIQUID CRYSTAL DISPLAY DEVICE COMPRISING THE SAME

CROSS REFERENCE TO RELATED APPLICATION

The present application claims priority to and the benefit of Korean patent application No. 2008-0089931 filed in the Korea Intellectual Property Office on Sep. 11, 2008, the entire content of which is incorporated hereinto by reference.

BACKGROUND OF THE INVENTION

(a) Field of the Invention

The present invention relates to a novel pyran derivative, its preparation method, a liquid crystal composition and a liquid crystal display device comprising the same.

(b) Description of the Related Art

Liquid crystal compounds are widely used for various liquid crystal display devices applied for a watch, a notebook computer, a mobile phone, television and a monitor, etc., and demands therefor rapidly increase every year. Liquid crystal compounds used for the liquid crystal display devices include nematic liquid crystal phase, smectic liquid crystal phase and cholesteric liquid crystal phase, and nematic liquid crystal phase is most widely used. And, rather than using a single liquid crystal compound, various liquid crystal compounds are used in combination to satisfy physical properties required for various liquid crystal display devices.

More specifically, a liquid crystal composition comprising liquid crystal compounds should be stable to moisture, light, heat, air and electric fields, and chemically stable with each other under used environment, and it should have excellent compatibility with other liquid crystal compounds.

And, in order to be applied for a liquid crystal display device, a liquid crystal compound should have balanced physical properties of wide liquid crystal phase temperature range, appropriate refractive anisotropy ($\Delta n$) and dielectric anisotropy ($\Delta \epsilon$), viscosity and conductivity, etc. And, since required physical properties vary depending on the kinds of liquid crystal display devices, novel liquid crystal compounds that can be well mixed with various liquid crystal compounds to satisfy various physical properties depending on liquid crystal display device are continuously demanded.

SUMMARY OF THE INVENTION

The present invention provides a novel pyran derivative which has physical properties such as optical anisotropy, liquid crystal transition temperature, and dielectric anisotropy, etc. appropriate for a liquid crystal compound, and has excellent compatibility with other liquid crystal compounds, and thus, can be preferably used for the formation of a liquid crystal layer of various liquid crystal display devices.

Further, the present invention provides a method for preparing the pyran derivative.

The present invention also provides a liquid crystal composition and a liquid crystal display device comprising the pyran derivative.

The present invention provides a pyran derivative of the following Chemical Formula I:

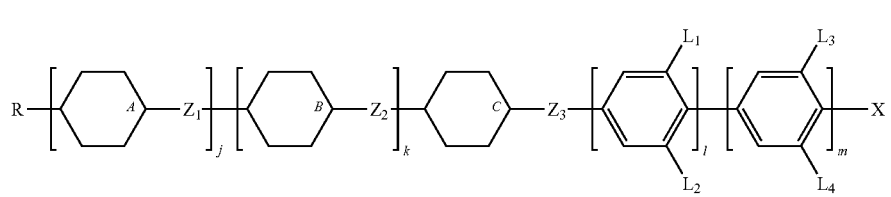

Wherein
R is H, $C_1$~$C_{15}$ alkyl, $C_2$~$C_{15}$ alkenyl group or $R_1O$—; $R_1$ is H, $C_1$~$C_{15}$ alkyl or $C_2$~$C_{15}$ alkenyl group;
ring C is

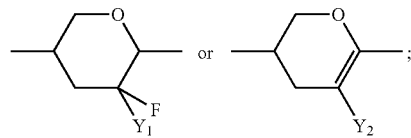

ring A and ring B are independently

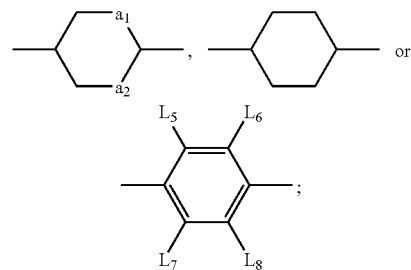

$Y_1$ is H, F, Cl, CN or $CF_3$; $Y_2$ is F, Cl, CN or $CF_3$; $a_1$ and $a_2$ are independently O or N;
$Z_1$, $Z_2$ and $Z_3$ are independently —$(CH_2)_n$— (n is 0 or 2), —C≡C—, —C(=O)O—, —OC(=O)—, —$CF_2$O—, —$OCF_2$—, —OC(=O)O—, —$CH_2$O—, —$CH_2$C(=O)—, —$OCH_2$— or —C(=O)$CH_2$—;
X is Cl, F, $CF_3$, $OCF_3$, $OCHF_2$, $CHF_2$, $CH_2F$, $OCF_2CHF_2$ or $OCF_2CHFCH_3$;
$L_1$ to $L_8$ are independently H or F; and,
j, k, l, and m are independently 0, 1 or 2.

The present invention also provides a method for preparing a pyran derivative comprising the steps of: cyclizing a compound of the following Chemical Formula II to form a compound of the following Chemical Formula III; and forming a pyran derivative of the Chemical Formula I from the compound of the Chemical Formula III:

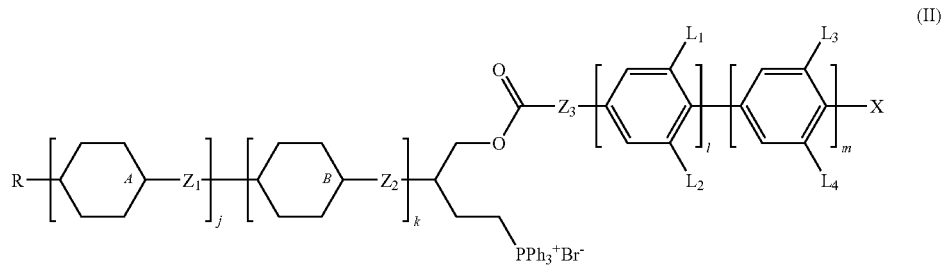

(II)

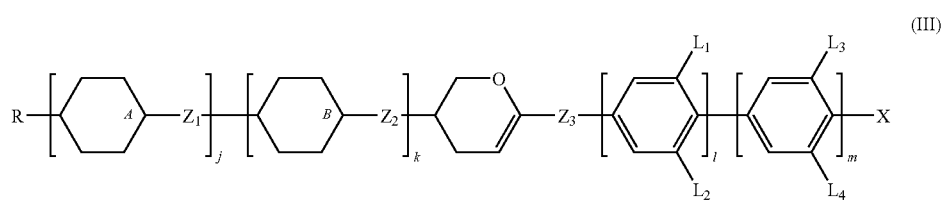

(III)

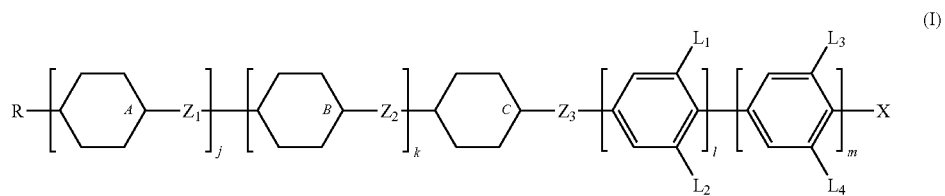

(I)

Wherein, R, rings A to C, $Z_1$ to $Z_3$, $L_1$ to $L_4$, j, k, l and m are as defined above.

The present invention also provides a liquid crystal composition comprising one or more kinds of the pyran derivatives.

The present invention also provides a liquid crystal display device which comprises a liquid crystal layer comprising the liquid crystal composition.

DETAILED DESCRIPTION OF THE EMBODIMENTS

A pyran derivative, its preparation method, a liquid crystal composition and a liquid crystal display device comprising the same according to embodiments of the invention will now be explained in detail.

According to one embodiment of the invention, a pyran derivative of the following Chemical Formula I is provided:

Wherein

R is H, $C_1$~$C_{15}$ alkyl, $C_2$~$C_{15}$ alkenyl group or $R_1O$—; $R_1$ is H, $C_1$~$C_{15}$ alkyl or $C_2$~$C_{15}$ alkenyl group;

ring C is

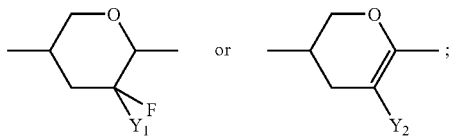

ring A and ring B are independently

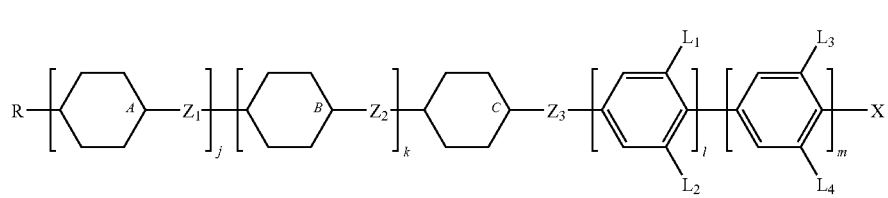

(I)

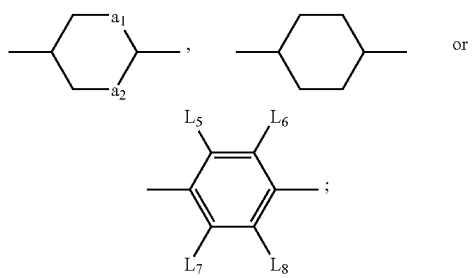

$Y_1$ is H, F, Cl, CN or $CF_3$; $Y_2$ is F, Cl, CN or $CF_3$; $a_1$ and $a_2$ are independently O or N;

$Z_1$, $Z_2$ and $Z_3$ are independently —$(CH_2)_n$— (n is 0 or 2), —C≡C—, —C(=O)O—, —OC(=O)—, —$CF_2$O—, —$OCF_2$—, —OC(=O)O—, —$CH_2$O—, —$CH_2$C(=O)—, —$OCH_2$— or —C(=O)$CH_2$—;

X is Cl, F, $CF_3$, $OCF_3$, $OCHF_2$, $CHF_2$, $CH_2F$, $OCF_2CHF_2$ or $OCF_2CHFCH_3$;

$L_1$ to $L_8$ are independently H or F; and, j, k, l, and m are independently 0, 1 or 2.

As results of experiments of the inventors, it has been found that said pyran derivative manifests appropriate refractive anisotropy (optical anisotropy) and liquid crystal transition temperature and excellent dielectric anisotropy (high positive dielectric anisotropy), and thus can be preferably used for a liquid crystal compound for the formation of a liquid crystal layer of a liquid crystal display device.

Especially, said pyran derivative manifests nematic liquid crystallinity over wide temperature range as well as appropriate optical anisotropy and high positive dielectric anisotropy, and has excellent compatibility with each other or with other liquid crystal compounds, and thus, when mixed with various liquid crystal compounds, it can satisfy various physical properties required for various liquid crystal display devices.

Accordingly, said pyran derivative can be used for various liquid crystal display devices and it can be used to provide a liquid crystal composition having nematic liquid crystallinity over a wide temperature range, appropriate optical anisotropy and low threshold voltage, and the liquid crystal composition can be used to provide various liquid crystal display devices having short response time, low power consumption, large contrast and high voltage holding ratio.

Meanwhile, in the pyran derivative according to one embodiment of the invention, $C_2$~$C_{15}$ alkenyl group of R or $R_1$ may be commonly known $C_2$~$C_5$ alkenyl group, for examples, —CH=$CH_2$, —CH=$CHCH_3$ (E,Z), —$CH_2$CH=$CH_2$, —CH=$CHCH_2CH_3$ (E,Z), —$CH_2$CH=$CHCH_3$ (E,Z), —$CH_2CH_2$CH=$CH_2$, —CH=$CHCH_2CH_2CH_3$ (E,Z), —$CH_2$CH=$CHCH_2CH_3$ (E,Z), —$CH_2CH_2$CH=$CHCH_3$ (E,Z) or —$CH_2CH_2CH_2$CH=$CH_2$.

And, in the case where the ring A or the ring B is 1,4-cyclohexyl

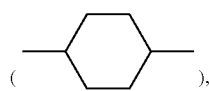

or the ring C is 2,5-tetrahydropyran

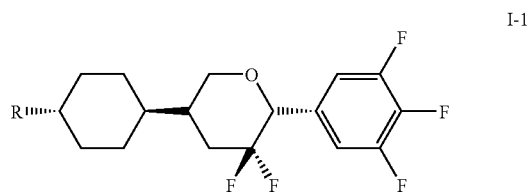

the 1,4-cyclohexyl or 2,5-tetrahydropyran is preferably in the form of trans-stereoisomer. And, in the case where the 2,5-tetrahydropyran of the ring C has only one fluorine substituted therefor (i.e., $Y_1$ is not fluorine), the fluorine is preferably bonded in an equatorial position.

When the pyran derivative has the above chemical structure, physical properties required for pyran derivative, for examples, appropriate optical anisotropy and liquid crystal transition temperature, and high positive dielectric anisotropy, etc. can be optimized and thus it can be preferably used as a liquid crystal compound for a liquid crystal display device.

Concrete examples of the pyran derivative of the Chemical Formula I includes compounds of the following Chemical Formulae I-1 to I-70, which can be preferably used as a liquid crystal compound for a liquid crystal display device:

I-1

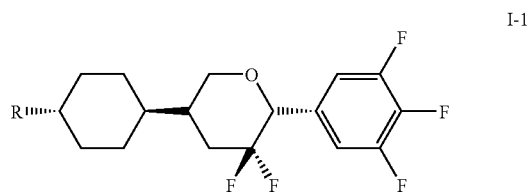

I-2

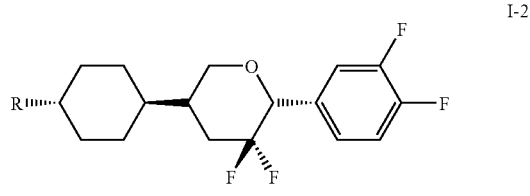

I-3

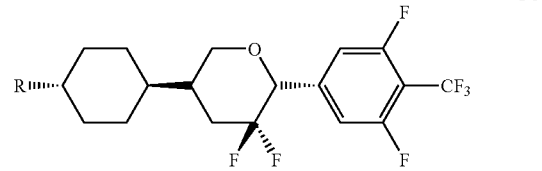

I-4

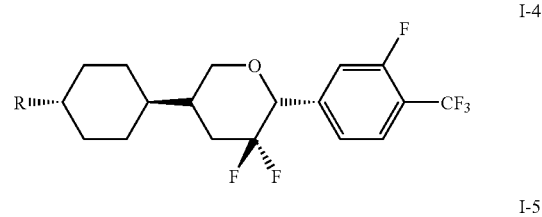

I-5

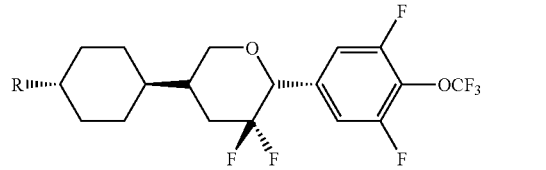

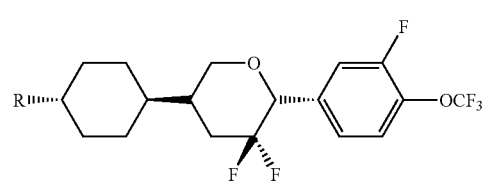 I-6
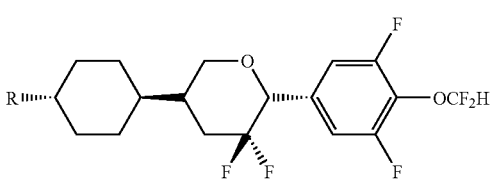 I-7
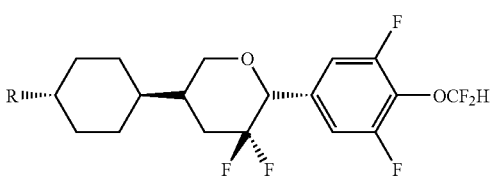 I-8
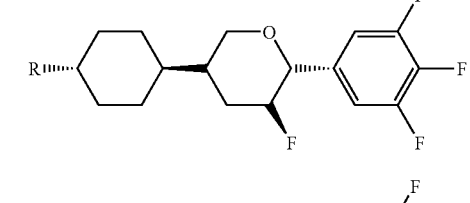 I-9
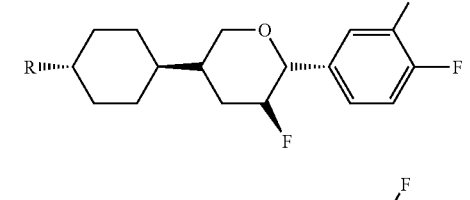 I-10
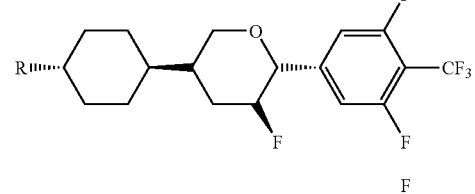 I-11
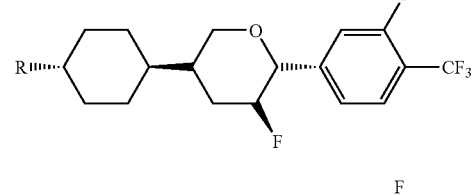 I-12
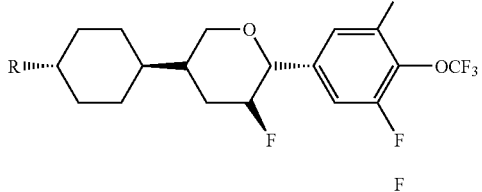 I-13
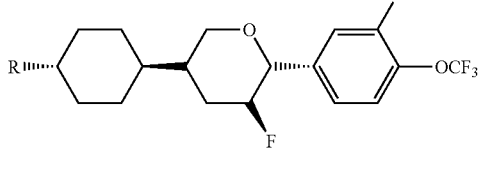 I-14
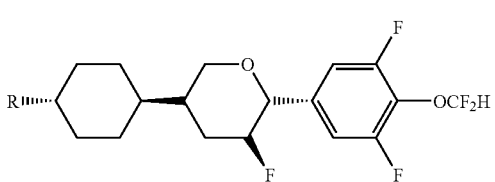 I-15
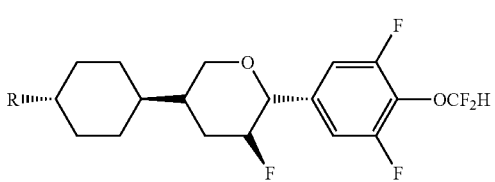 I-16
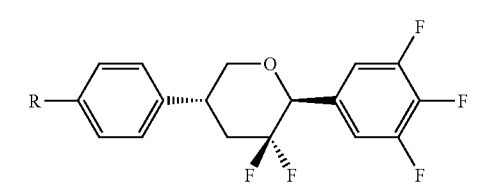 I-17
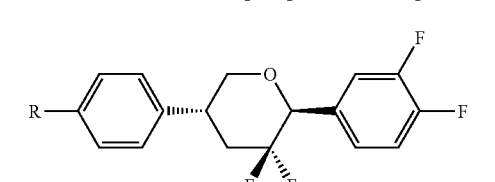 I-18
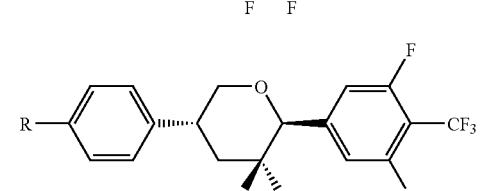 I-19
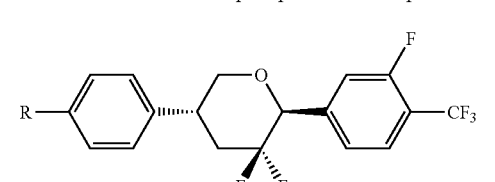 I-20
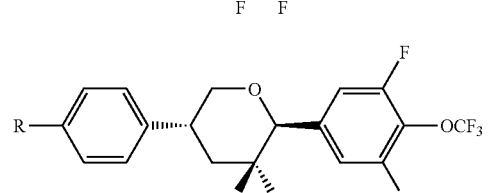 I-21
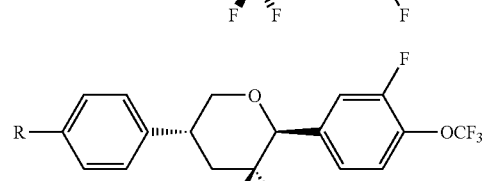 I-22
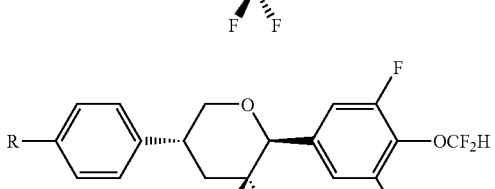 I-23

I-24
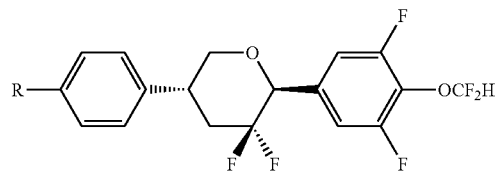
I-25
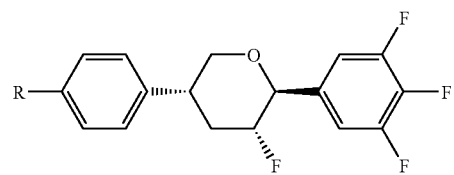
I-26
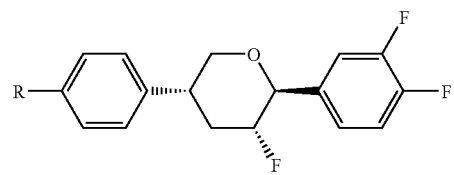
I-27
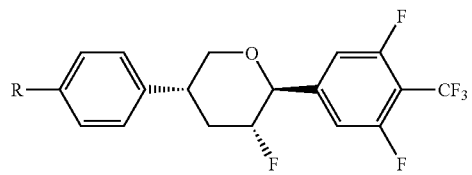
I-28
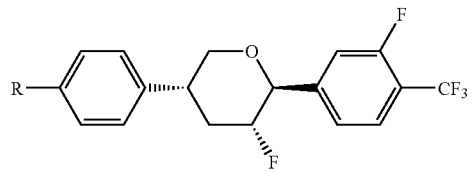
I-29
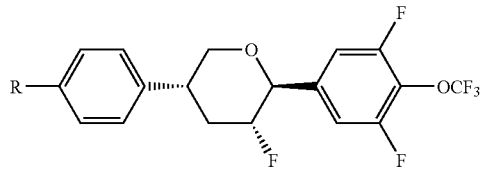
I-30
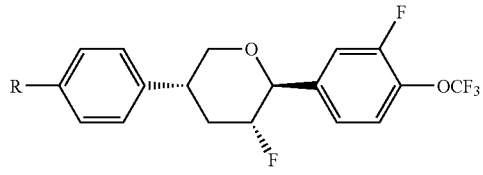
I-31
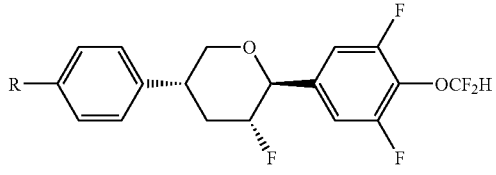
I-32
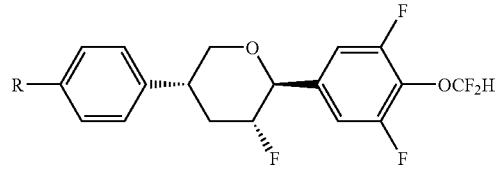
I-33
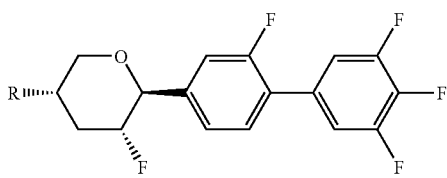
I-34
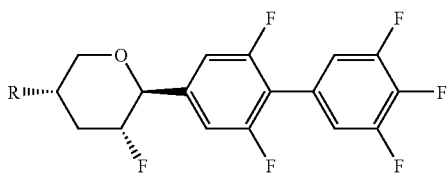
I-35
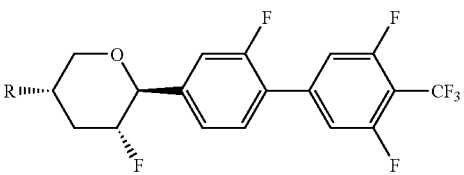
I-36
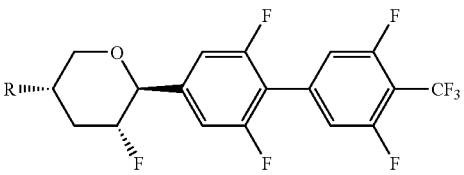
I-37
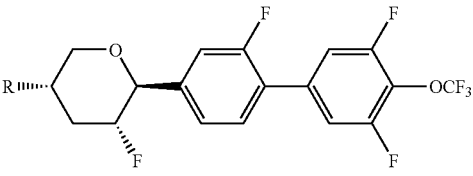
I-38
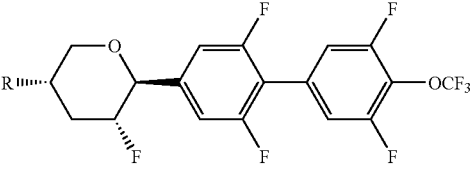
I-39
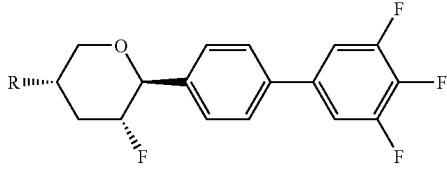
I-40
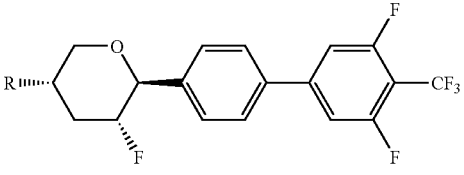
I-41
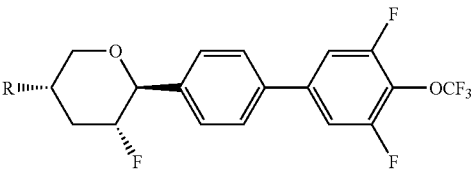

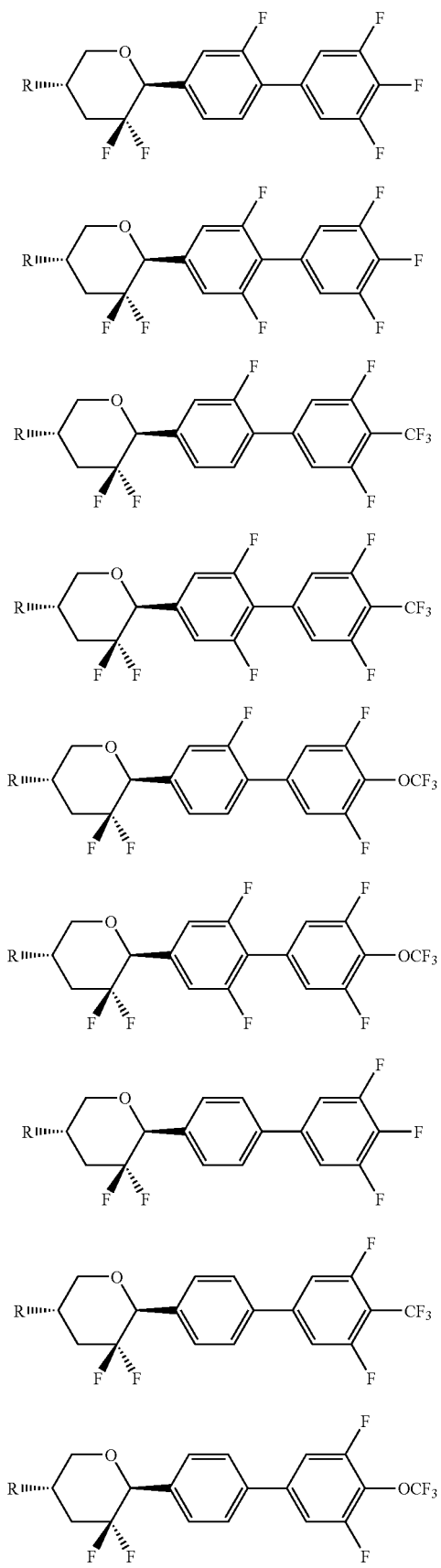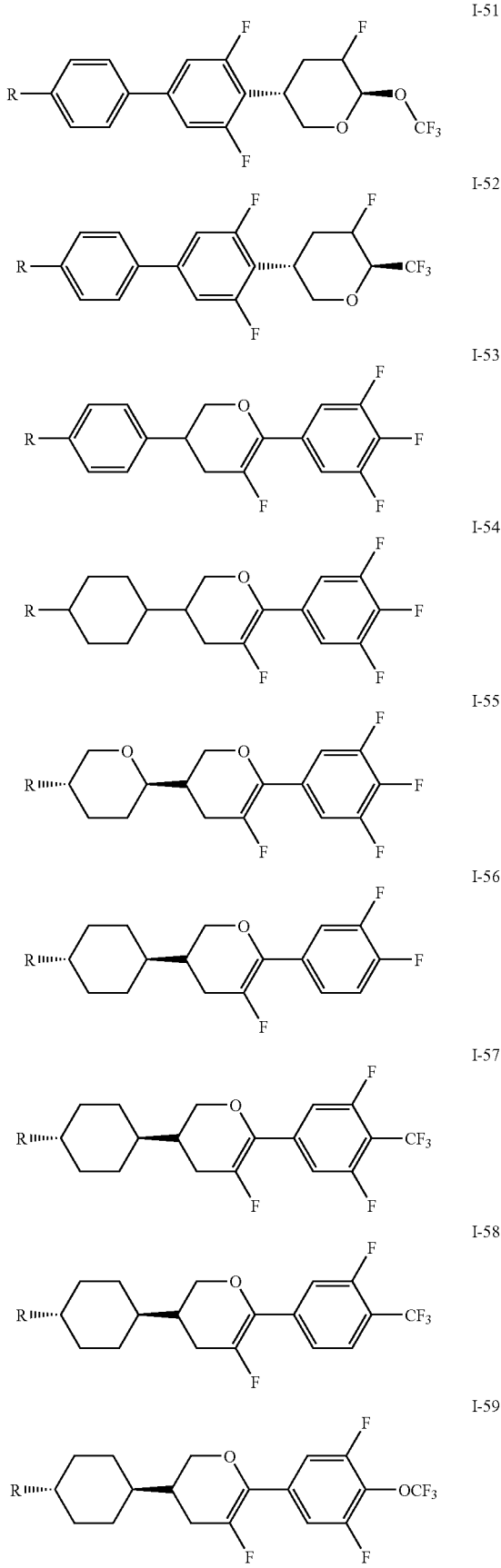

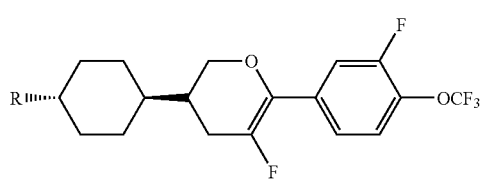 I-60

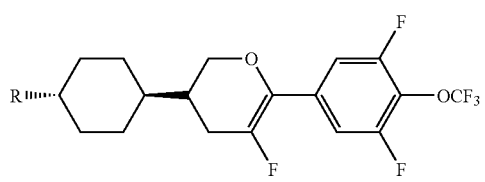 I-61

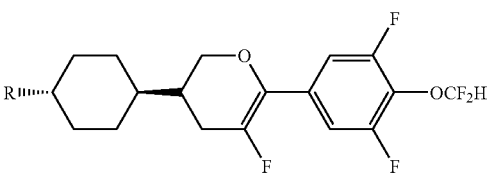 I-62

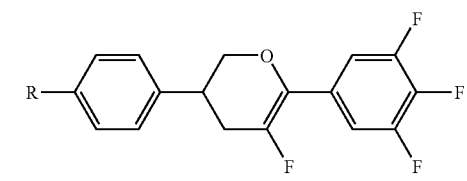 I-63

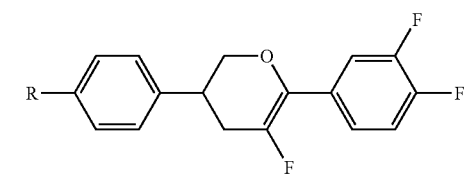 I-64

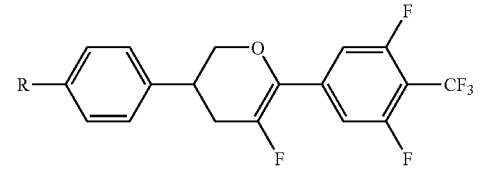 I-65

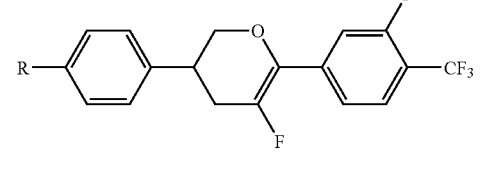 I-66

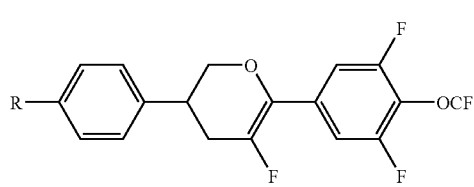 I-67

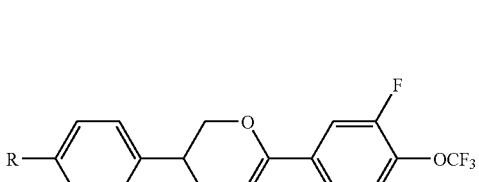 I-68

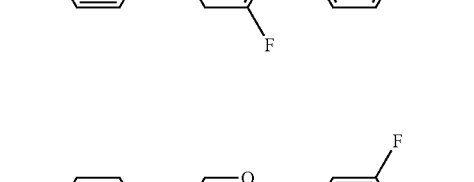 I-69

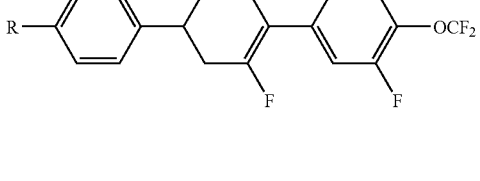 I-70

However, in addition to the compounds of the above Chemical Formulae I-1 to I-70, various pyran derivatives falling within the range of the Chemical Formula I can be preferably used as a liquid crystal compound for the formation of a liquid crystal layer of various liquid crystal display devices.

According to another embodiment of the invention, a method for preparing the pyran derivative of the Chemical Formula I is provided. The method comprises the steps of cyclizing a compound of the following Chemical Formula II to form a compound of the following Chemical Formula III; and forming a pyran derivative of the Chemical Formula I from the compound of the Chemical Formula III:

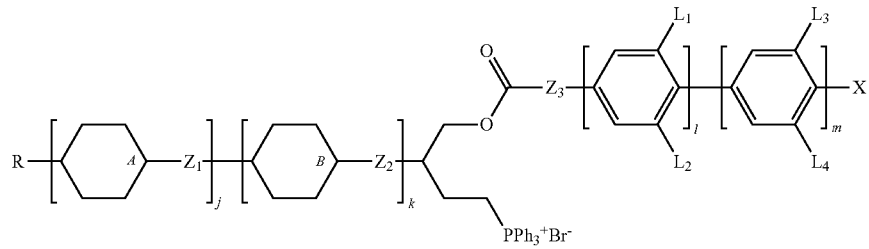 (II)

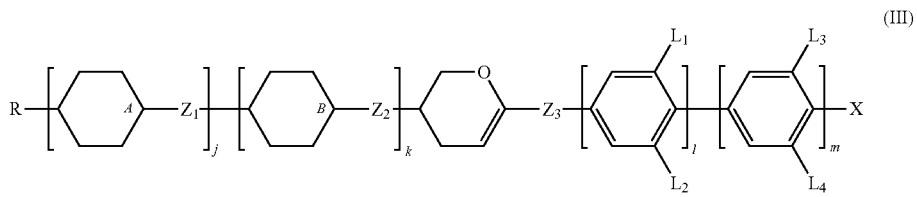

Wherein, R, rings A to C, $Z_1$ to $Z_3$, $L_1$ to $L_4$, j, k, l and m are as defined above.

In the above method, the compound of the Chemical Formula II can be prepared from known compounds by any methods obviously known in the art as will be described in the Examples.

And, in the above method, the compound of the Chemical Formula III is formed by cyclization of the compound of the Chemical Formula II, and said cyclization can be conducted in the presence of base such as NaHMDS (sodium hexamethyldisilazide) under common reaction conditions and can be conducted in an organic solvent such as THF.

And, after formation of the compound of the Chemical Formula III, substituent $Y_1$ and fluorine, or substituent $Y_2$ are introduced therein to prepare said pyran derivative of the Chemical Formula I. The introduction of the substituents is carried out according to common reaction conditions and methods depending on the kinds of the substituent.

For example, in the step of forming the pyran derivative of the Chemical Formula I, a compound of the Chemical Formula III is fluorinated to form a compound of the following Chemical Formula IV which falls within the range of the above Chemical Formula I:

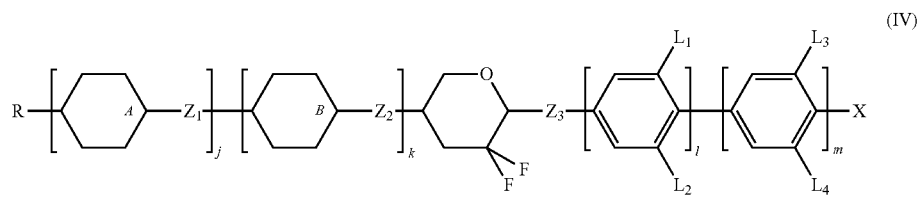

Wherein, R, rings A to C, $Z_1$ to $Z_3$, $L_1$ to $L_4$, j, k, l and m are as defined above.

More specifically, for the fluorination, hydroboration and oxidation of the compound of the Chemical Formula III are conducted to form a compound of the following Chemical Formula VII, which is then fluorinated to form a compound of the Chemical Formula IV. The hydroboration, oxidation and fluorination are carried out under common reaction conditions as will be described in the Example:

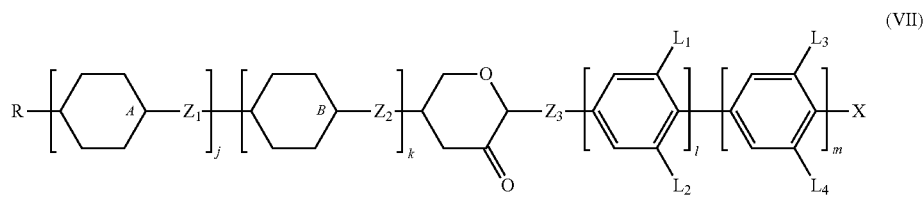

Wherein, R, rings A to C, $Z_1$ to $Z_3$, $L_1$ to $L_4$, j, k, l and m are as defined above.

Meanwhile, the step of forming the pyran derivative of the Chemical Formula I may further comprise, after forming the compound of the Chemical Formula IV, the step of defluorinating it to form a compound of the following Chemical Formula V:

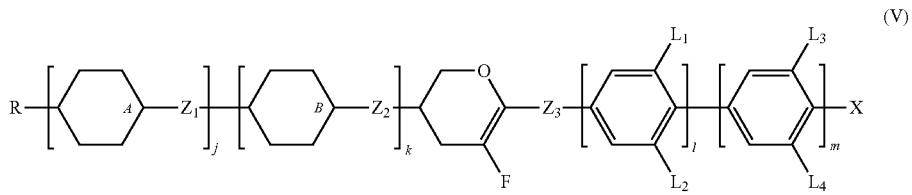

Wherein, R, rings A to C, $Z_1$ to $Z_3$, $L_1$ to $L_4$, j, k, l and m are as defined above.

And, the step of forming the pyran derivative of the Chemical Formula I may further comprise, after forming the compound of the Chemical Formula V, the step of hydrogenating (reducing) it to form a compound of the following Chemical Formula VI:

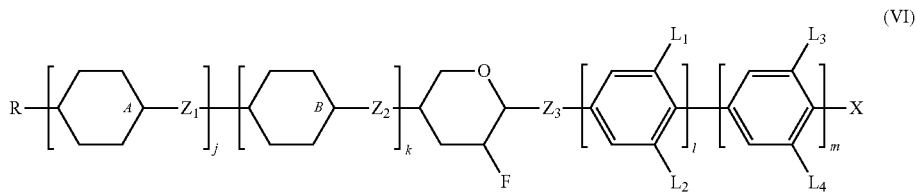

Wherein, R, rings A to C, $Z_1$ to $Z_3$, $L_1$ to $L_4$, j, k, l and m are as defined above.

Through the above processes, various compounds falling within the range of the Chemical Formula I, for examples, the compound of the Chemical Formula V or VI can be prepared. The reactions are carried out according to common reaction conditions and methods depending on the reaction.

According to the above explained method, various pyran derivatives falling within the range of the Chemical Formula I can be prepared, and, in addition, depending on the kinds of the substituents of $Y_1$ and $Y_2$, common substituent introduction can be conducted for the compounds of the Chemical Formulae III to VII to prepare the pyran derivative of the Chemical Formula I.

According to another embodiment of the invention, a liquid crystal composition comprising one or more kinds of the above pyran derivatives of the Chemical Formula I is provided. Since the liquid crystal composition comprises a liquid crystal compound manifesting appropriate optical anisotrotpy and liquid crystal transition temperature and high positive dielectric anisotropy, it can be preferably used for a liquid crystal composition for the formation of a liquid crystal layer of a liquid crystal display device, for example, nematic liquid crystal composition.

Especially, since the liquid crystal composition may comprise one or more kinds of liquid crystal compounds including the pyran derivative of the Chemical Formula I to satisfy various physical properties required for various liquid crystal display devices, it can be used for the formation of a liquid crystal layer of various liquid crystal display devices, and it can manifest preferable physical properties therefor, for examples, nematic liquid crystallinity over a wide temperature range, appropriate optical anisotropy and lower threshold voltage, etc.

Therefore, the liquid crystal composition can be used to provide various liquid crystal display devices having short response time, low power consumption, large contrast, and high voltage holding ratio.

Meanwhile, the liquid crystal composition may comprise two or more kinds of the pyran derivatives of the Chemical Formula I, or it may comprise one or more kinds of other commonly used liquid crystal compounds together with one or more kinds of the pyran derivatives of the Chemical Formula I. The liquid crystal composition may comprise 1 to 50 wt % of each pyran derivative of the Chemical Formula I, based on the total weight of the liquid crystal composition.

Thereby, a liquid crystal composition having appropriately controlled physical properties required for various liquid crystal display devices can be easily provided.

And, the liquid crystal composition may comprise one or more kinds of pyran derivatives wherein the ring A or the ring B in the Chemical Formula I 1,4-cyclohexyl

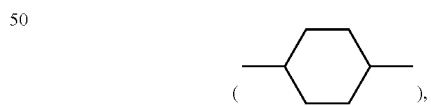

or the ring C is 2,5-tetrahydropyran

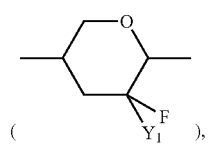

and said pyran derivative preferably comprises a compound wherein the 1,4-cyclohexyl or 2,5-tetrahydropyran is in the form of trans-stereoisomer and a compound wherein the 1,4- cyclohexyl or 2,5-tetrahydropyran is in the form of cis-stereoisomer in a mole ratio of 85:15 or more, more preferably 95:5 or more, most preferably 100:0.

And, in the pyran derivative, in the case where the 2,5-tetrahydropyran of the ring C has only one fluorine substituted therefor (i.e., $Y_1$ is not fluorine), the fluorine is preferably bonded in an equatorial position.

If the liquid crystal composition comprises pyran derivatives in the form of stereoisomers as described above, various physical properties of a liquid crystal composition, for examples, appropriate optical anisotropy and liquid crystal transition temperature and high positive dielectric anisotropy, etc. can be further optimized and thus it can be preferably used for the formation of a liquid crystal layer of a liquid crystal display device.

The liquid crystal composition may comprise one or more kinds of other commonly known liquid crystal compounds together with one or more kinds of the pyran derivatives of the Chemical Formula I. And, the compositional ratio of each liquid crystal compound can be determined by one or ordinary skill in the art considering the kind of liquid crystal display device to be applied, physical properties required for a liquid crystal composition, etc.

And, if necessary, the liquid crystal composition may comprise appropriate additives, and the additives are obviously known to be usable in a liquid crystal composition for the formation of a liquid crystal layer of a liquid crystal display device. For example, the liquid crystal composition may comprise any additives described in "H. Kelker/R. Hatz, Handbook of Liquid Crystals, Verlag Chemie, Weinheim, 1980".

More specifically, the liquid crystal composition may further comprise additives for modifying dielectric anisotropy, viscosity and/or arranged direction of nematic liquid crystal phase. For example, it may comprise chiral dopants for inhibiting spiral structure and reverse twist of liquid crystal, or dichroic pigment.

Meanwhile, according to another embodiment of the invention, a liquid crystal display device which comprises a liquid crystal layer comprising the above described liquid crystal composition is provided.

The liquid crystal display device may be any liquid crystal display devices known so far, for examples, simple matrix type twisted nematic liquid crystal display, simple matrix type supertwisted nematic liquid crystal display, active TFT liquid crystal display, active MIM liquid crystal display, active IPS liquid crystal display, etc.

And, the liquid crystal display device can be prepared using the above explained liquid crystal composition by common method known in the art. For example, the liquid crystal display can be prepared by dissolving the liquid crystal composition at an appropriate temperature, and then introducing it in a position where a liquid crystal layer of a liquid crystal display device is to be formed. Wherein, using appropriate additives, a liquid crystal layer of a liquid crystal display can be formed using the liquid crystal composition.

EXAMPLES

The present invention will be explained with reference to the following Examples. However, these examples are only to illustrate the invention, and the scope of the invention is not limited thereto.

Example 1

Synthesis of Liquid Crystal Compounds of Formula I-20a

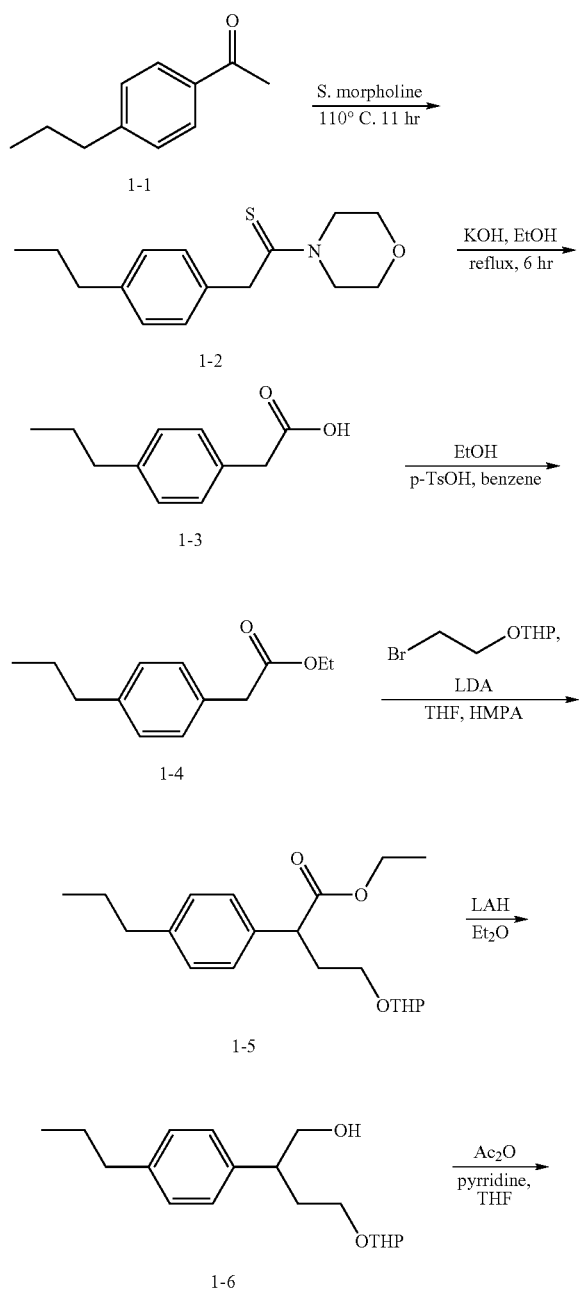

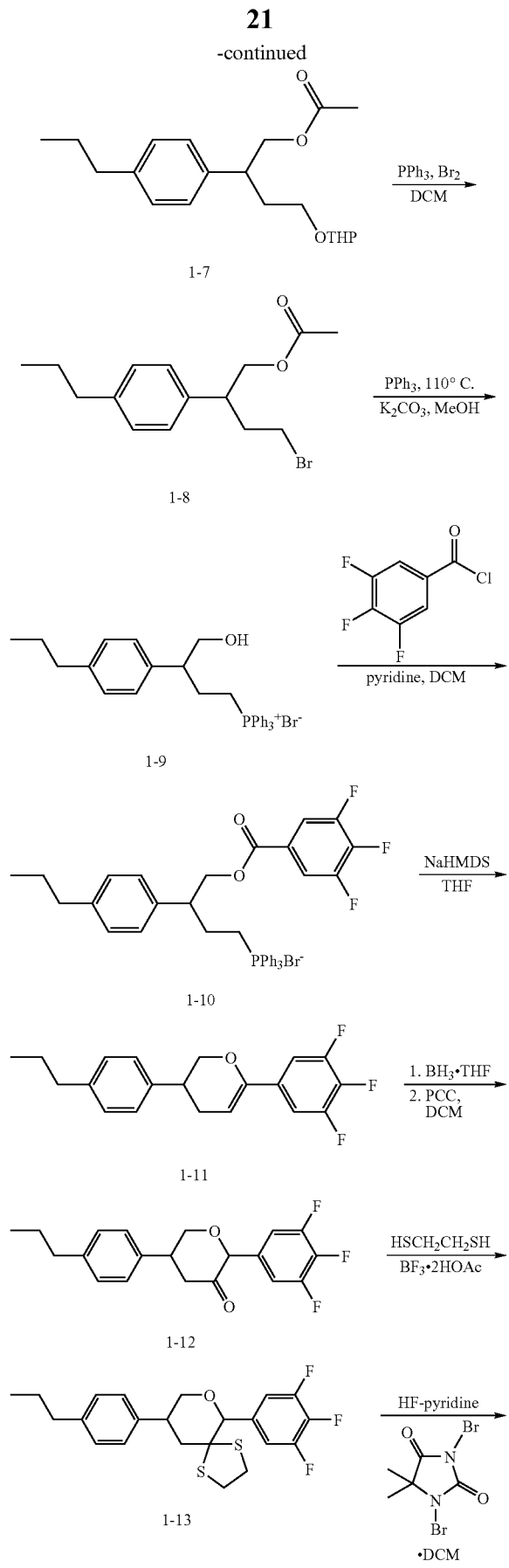
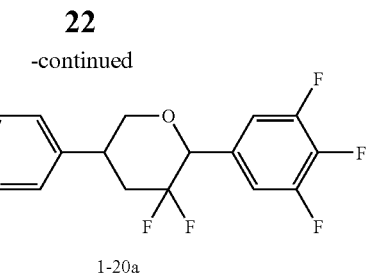

(Step 1)

10.0 g of 4-n-propylacetophenone (compound 1-1), 3.95 g of sulfur and 0.74 g of morpholine were introduced into a flask, and the mixture was reacted at 110° C. for 12 hours. Then, temperature of the reaction mixture was lowered to a room temperature, and it was poured into 30 mL of MeOH. Thus prepared solution was maintained at 0° C. to precipitate solids, the precipitated solids were filtered, and the filtered solids were washed with cold MeOH. And, MeOH was dried to obtain a compound 1-2.

500 MHz $^1$H-NMR (CDCl$_3$) δ (ppm): 0.92 (t, 3H), 1.61 (sex, 2H), 2.56 (t, 2H), 3.39 (m, 2H), 3.63 (m, 2H), 3.74 (m, 2H), 4.32 (s, 2H), 4.35 (m, 2H), 7.12 (d, 2H), 7.21 (d, 2H).

(Step 2)

To the compound 1-2, 42.0 g of 50% KOH aqueous solution and 72 mL of EtOH were added, and the mixed solution was heat-refluxed for 6 hours. 65 Ml of EtOH were removed from the reaction solution, temperature of the solution was lowered to 0° C., and the formed solids were filtered and removed. To the solid-removed solution, HCl was added to control pH thereof to 1. The formed solids were filtered, washed with cold water, and dried to obtain a compound 1-3.

500 MHz $^1$H-NMR (CDCl$_3$) δ (ppm): 0.94 (t, 3H), 1.62 (sex, 2H), 2.56 (t, 2H), 3.60 (s, 2H), 7.13 (d, 2H), 7.18 (d, 2H).

(Step 3)

To a solution of the compound 1-3 dissolved in 17 mL of EtOH and 5 mL of benzene, 3.52 g of p-TsOH was added. To a flask containing the mixed solution, a vigreux column was installed, and the mixed solution was boiled until water was removed. And then, benzene and a part of EtOH were removed by distillation, and the reaction solution was heat-refluxed again for a determined time. Charcoal was mixed with the reaction solution and the solution was filtered, and the filtered solution was concentrated. A compound 1-4 was separated by silica gel column chromatography.

500 MHz $^1$H-NMR (CDCl$_3$) δ (ppm): 0.94 (t, 3H), 1.25 (t, 3H), 1.61 (sex, 2H), 2.56 (t, 2H), 3.58 (s, 2H), 4.14 (q, 2H), 7.13 (d, 2H), 7.19 (d, 2H).

(Step 4)

Temperature of a mixed solution of 36.97 mL of nBuLi (2.5M in hexane) and 50 mL of anhydrous THF was lowered to 0° C., and to the mixed solution, 16.19 mL of diisopropylamine was slowly added and the solution was further reacted for 15 minutes while maintaining 0° C. Temperature of the prepared mixed solution was lowered to −78° C., and 15.89 g of the compound 1-4 was added, and then, the mixture was reacted for 30 minutes. While maintaining temperature of the solution at −78° C., a solution of 17.72 g of THP-protected bromoethaneol dissolved in 15 mL of hexamethylphosphoamide (HMPA) was slowly added thereto. Thus prepared reaction solution was further reacted at −78° C. for 10 minutes, and then, temperature of the solution was elevated to a room temperature, and the solution was reacted for 20 hours. To the reaction solution, ice water was added to complete the reaction, and a water layer was extracted using ether. An organic layer was washed with distilled water and saturated brine, and dried with MgSO$_4$. A compound 1-5 was obtained using column chromatography.

500 MHz $^1$H-NMR (CDCl$_3$) δ (ppm): 0.93 (t, 3H), 1.22 (t, 3H), 1.50~1.71 (m, 7H), 1.81 (m, 1H), 2.01 (sep, 1H), 2.35 (sex, 1H), 2.55 (t, 2H), 3.23~3.37 (m, 1H), 3.45 (m, 1H), 3.67~3.84 (m, 3H), 4.05~4.15 (m, 2H), 4.48~4.55 (m, 1H), 7.12 (d, 2H), 7.21 (d, 2H).

(Step 5)

Temperature of a mixed solution of 2.17 g of LAH and anhydrous diethylether was lowered to 0° C., and to the solution, a solution of 15.93 g of the compound 1-5 dissolved in anhydrous ether was added. The reaction solution was heat-refluxed for 2 hours, and the temperature was lowered to 0° C. again, and then, 2 mL of water, 4 mL of 15% NaOH and 6 mL of water were sequentially added to complete the reaction, and a water layer was extracted using ether. An extracted organic layer was washed with NH$_4$Cl saturated aqueous solution, and dried with MgSO$_4$, and then, a compound 1-6 was obtained using column chromatography.

500 MHz $^1$H-NMR (CDCl$_3$) δ (ppm): 0.94 (t, 3H), 1.50~2.07 (m, 10H), 2.57 (t, 2H), 2.95 (m, 1H), 3.28~3.40 (m, 1H), 3.46 (m, 1H), 3.67~3.72 (m, 4H), 4.49~4.57 (m, 1H), 7.13 (s, 4H).

(Step 6)

To a solution of 12.78 g of the compound 1-6 dissolved in anhydrous THF, 24.74 mL of pyridine was added, and subsequently, 12.39 mL of anhydrous acetic acid was added and the solution was reacted for 3 hours. The reaction solution was diluted with ether, and then, the temperature was lowered to 0° C. and 1N HCl was added thereto. The solution was extracted using ether, and the extract organic layer was washed with water, NaHCO$_3$ aqueous solution and saturated brine sequentially, and dried with MgSO$_4$, and a compound 1-7 was obtained using column chromatography.

500 MHz $^1$H-NMR (CDCl$_3$) δ (ppm): 0.93 (t, 3H), 1.48~1.89 (m, 9H), 2.00 (s, 3H), 2.06 (m, 1H), 2.55 (t, 2H), 3.07 (m, 1H), 3.21~3.29 (m, 1H), 3.41 (m, 1H), 3.61~3.68 (m, 2H), 4.19 (m, 2H), 4.22~4.52 (m, 1H), 7.10 (s, 4H).

(Step 7)

Temperature of a solution of 23.62 g of PPh$_3$ dissolved in DCM was lowered to −15° C., and to the solution, 4.61 mL of Br$_2$ was added. Subsequently, to the mixed solution, a solution of 13.69 g of the compound 1-7 dissolved in dichloromethane (DCM) was added and the solution was reacted at room temperature for 20 hours. The reaction solution was washed with distilled water and saturated brine, and dried with MgSO$_4$. A compound 1-8 was obtained using column chromatography.

500 MHz $^1$H-NMR (CDCl$_3$) δ (ppm): 0.94 (t, 3H), 1.62 (sex, 2H), 2.03 (s, 3H), 2.16 (m, 1H), 2.28 (m, 1H), 2.56 (t, 2H), 3.14 (m, 2H), 3.33 (m, 1H), 4.17 (m, 1H), 4.23 (m, 1H), 7.12 (m, 4H).

(Step 8)

9.92 g of PPh$_3$ and 9.87 g of the compound 1-8 were mixed, and the mixture was heated to 110° C. and reacted for 24 hours. The reaction mixture was dissolved in 100 mL of MeOH, and to the solution, a solution of 0.26 g of K$_2$CO$_3$ dissolved in 10 mL of water was added and the mixed solution was reacted for 20 hours. A solvent was removed and a compound 1-9 was separated using column chromatography (ethylacetate/MeOH).

500 MHz $^1$H-NMR (CDCl$_3$) δ (ppm): 0.93 (t, 3H), 1.60 (sex, 2H), 1.97 (m, 1H), 2.34 (m, 1H), 2.54 (t, 2H), 3.30 (m, 1H), 3.45 (m, 1H), 3.89 (m, 3H), 4.47 (br, 1H), 7.04 (d, 2H), 7.07 (d, 2H), 7.63~7.78 (m, 15H).

(Step 9)

To a solution of 15.93 g of the compound 1-9 dissolved in DCM, 3.62 mL of pyridine was added. Temperature of the solution was lowered to 0° C., 4.30 mL of 3,4,5-trifluorobenzoyl chloride was added. The solvent was removed and a compound 1-10 was separated using column chromatography (ethyl acetate/MeOH).

500 MHz $^1$H-NMR (CDCl$_3$) δ (ppm): 0.91 (t, 3H), 1.62 (sex, 2H), 1.78 (m, 1H), 2.23 (m, 1H), 2.54 (t, 2H), 3.02 (m, 1H), 3.84 (m, 1H), 4.42 (m, 1H), 4.48 (m, 1H), 4.83 (m, 1H), 7.10 (d, 2H), 7.16 (d, 2H), 7.50 (m, 2H), 7.65 (m, 6H), 7.78 (m, 9H).

(Step 10)

Temperature of a solution of 10.0 g of the compound 1-10 dissolved in anhydrous THF was lowered to −78° C., and 28.9 mL of NaHMDS (1.0M in THF) was added thereto. The reaction solution was reacted at 40° C. for 3 hours, and then, further reacted at room temperature for 18 hours. Temperature of the reaction solution was lowered to 0° C., and the reaction was completed using an NH$_4$Cl aqueous solution. A water layer was extracted using ether, and an organic layer was washed sequentially with NH$_4$Cl saturated solution and saturated brine and dried with MgSO$_4$, and then, a compound 1-11 was obtained using column chromatography.

500 MHz $^1$H-NMR (CDCl$_3$) δ (ppm): 0.95 (t, 3H), 1.62 (sex, 2H), 2.46 (m, 2H), 2.58 (t, 2H), 3.10 (m, 1H), 3.97 (t, 1H), 4.34 (m, 1H), 5.46 (m, 1H), 7.12~7.21 (m, 6H).

(Step 11)

Temperature of a solution of 2.0 g of the compound 1-11 dissolved in anhydrous THF was lowered to 0° C., and 7.22 mL of borane THF (1.0M in THF) was added thereto. The reaction solution was heat-refluxed for 2 hours, and the temperature was lowered to a room temperature. To the solution, an ice water was added, and water layer was extracted using ether. The extracted organic layer was dried with MgSO$_4$ and concentrated. Thus obtained compound was dissolved in DCM again, and 0.1 g of 4 Å molecular sieves and 4.54 g of pyridinium chlorochromate (PCC) were added. The mixed solution was heat-refluxed for 4 hours, and cooled to a room temperature. The reaction solution was filtered with celite, and the solid-filtered solution was washed with saturated brine. The washed saturated brine solution was extracted again using DCM, and the organic layer washed with saturated brine and the extracted DCM solution were combined, and the mixture was washed with water and dried with MgSO$_4$. A compound 1-12 was obtained using column chromatography.

500 MHz $^1$H-NMR (CDCl$_3$) δ (ppm): 0.94 (t, 3H), 1.60 (sex, 2H), 2.56 (t, 2H), 2.86 (m, 2H), 3.19 (m, 1H), 3.89 (m, 1H), 4.26 (m, 1H), 4.92 (s, 1H), 7.15~7.23 (m, 6H).

(Step 12)

To a mixture of 1.82 g of the compound 1-12 and 0.88 mL of 1,2-ethanedithiol, 0.73 mL of borontrifluoride acetic acid was added. The reaction mixture was reacted at room temperature for 2 hours, and ether and water were sequentially added to complete the reaction. An water layer was extracted with ether, and an organic layer was washed sequentially with NaHCO$_3$ saturated aqueous solution, 10% NaOH aqueous solution and saturated brine and dried with MgSO$_4$. A compound 1-13 was obtained using column chromatography.

500 MHz $^1$H-NMR (CDCl$_3$) δ (ppm): 0.95 (t, 3H), 1.61 (sex, 2H), 2.56 (t, 2H), 2.65~2.88 (m, 6H), 2.95 (m, 1H), 3.94 (m, 1H), 4.31 (m, 1H), 5.32 (s, 1H), 7.15~7.23 (m, 6H).

(Step 13)

Temperature of a solution of 0.35 g of 1,2-dibromo-5,5-dimethyl hydantoin dissolved in anhydrous DCM was lowered to −78° C., and 1 cm$^3$ of HF-pyridine (70%-30%) was slowly added thereto. To the mixed solution, a solution of 0.5 g of the compound 1-13 dissolved in anhydrous DCM was slowly added for 30 minutes while maintaining the temperature at −78° C.~−60° C. The reaction solution was further reacted for 30 minutes while maintaining the temperature at −78° C. The reaction solution was filtered with basic alumina, and the solvent was removed, and then, a compound of the Chemical Formula I-20a was obtained using column chromatography.

500 MHz $^1$H-NMR (CDCl$_3$) δ (ppm): 0.95 (t, 3H), 1.61 (sex, 2H), 2.48 (m, 2H), 2.56 (t, 2H), 2.97 (m, 1H), 3.95 (m, 1H), 4.30 (m, 1H), 5.30 (s, 1H), 7.14~7.22 (m, 6H).

Example 2

Synthesis of Liquid Crystal Compounds of Formula I-53a

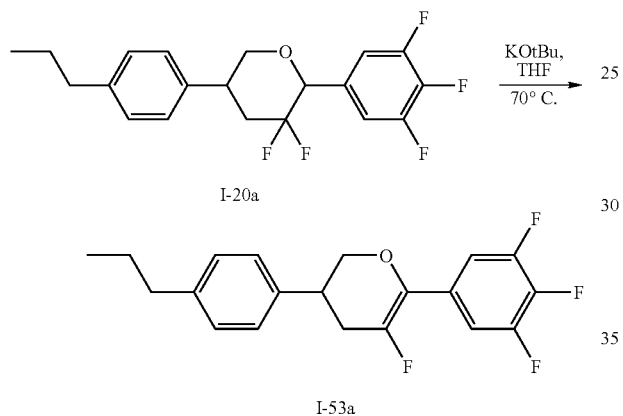

Temperature of a solution of 0.45 g of KOtBu dissolved in THF was lowered to 0° C., and a solution of 1.0 g of the compound 1-20a dissolved in THF was slowly added thereto. Temperature of the reaction solution was elevated to 70° C. and the solution was reacted for 5 hours. A compound of the Chemical Formula I-53a was obtained using ether work-up and column chromatography.

500 MHz $^1$H-NMR (CDCl$_3$) δ (ppm): 0.94 (t, 3H), 1.62 (sex, 2H), 2.47 (m, 2H), 2.57 (t, 2H), 3.09 (m, 1H), 3.96 (m, 1H), 4.34 (m, 1H), 7.13~7.22 (m, 6H).

Example 3

Synthesis of Liquid Crystal Compounds of Formula I-28a

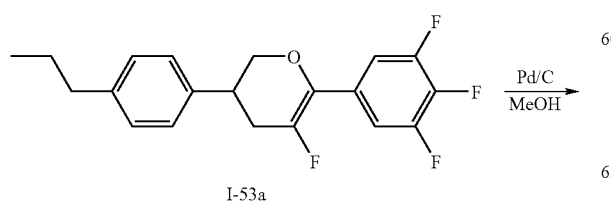

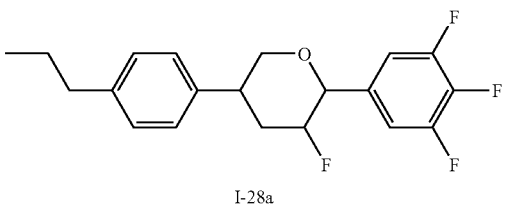

To a solution of 0.43 g of the compound 1-53a dissolved in MeOH, 0.13 g of 10% Pd/C was added, the reaction solution was reacted for 20 hours while maintaining the reaction flask under hydrogen atmosphere using a vacuum pump and hydrogen balloon. After the reaction was completed, Pd/C was filtered to remove, and the reaction solution was concentrated. A compound of the Chemical Formula I-28a was obtained using column chromatography.

500 MHz $^1$H-NMR (CDCl$_3$) δ (ppm): 0.94 (t, 3H), 1.61 (sex, 2H), 2.32 (m, 2H), 2.58 (t, 2H), 3.01 (m, 1H), 3.96 (t, 1H), 4.12 (m, 1H), 4.34 (m, 1H), 5.28 (m, 1H), 7.15~7.25 (m, 6H).

Example 4

Synthesis of Liquid Crystal Compounds of Formula I-4a

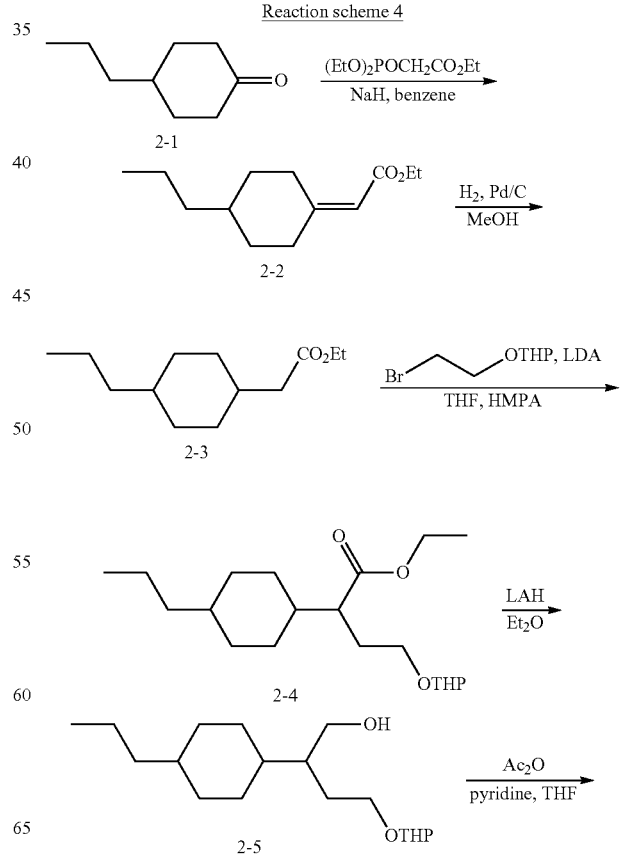

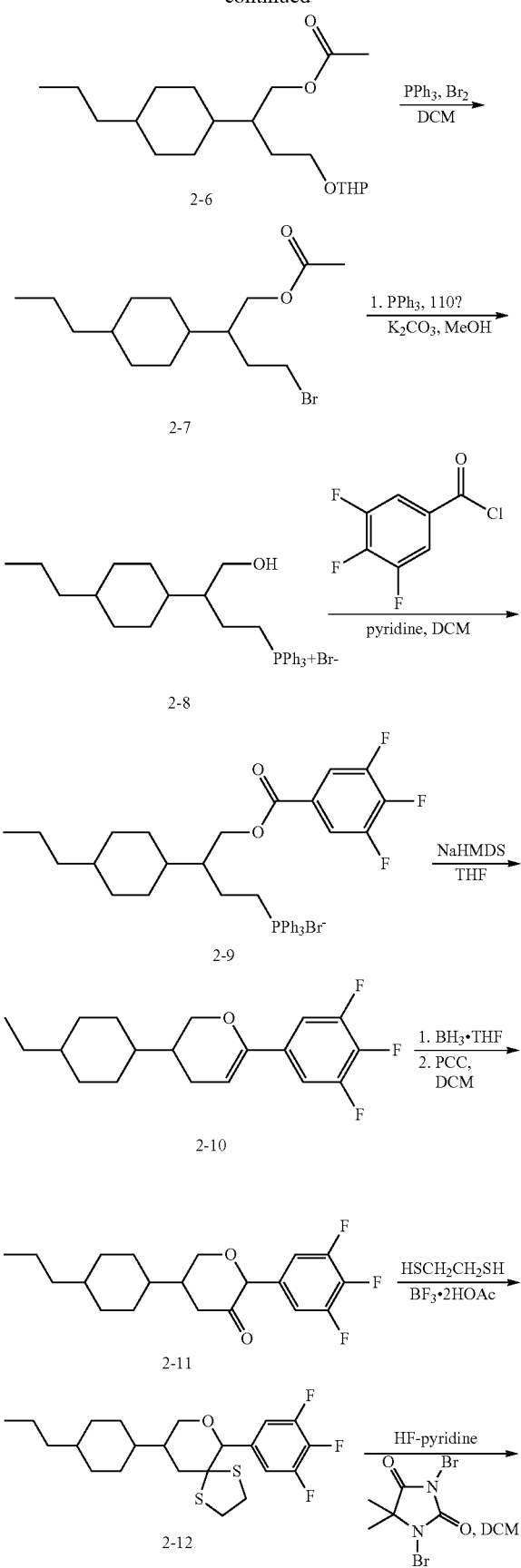

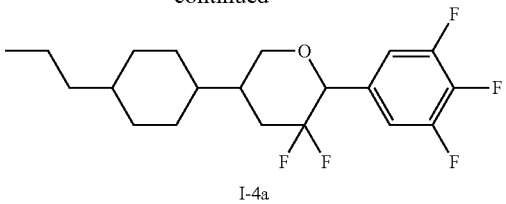

I-4a (Step 1)

To a mixture of 5.70 g of 60% NaH with benzene, 28.30 mL of triethylphosphonoacetate was slowly added over 50 minutes. During the addition, an ice bath was used so that temperature of the solution may not exceed 30° C. The mixed solution was reacted at room temperature for 1 hour. 20.0 g of 4-n-propylcyclohexanone (compound 2-1) was slowly added over 40 minutes. At this time, temperature of the solution was controlled so as not to exceed 25° C., and then, temperature of the reaction solution was elevated to 65° C. and the reaction solution was further reacted for 30 minutes. Temperature of the solution was lowered to a room temperature and the solution was extracted using ethyl acetate. Extracted organic solution was washed with distilled water and saturated brine, and dried with $MgSO_4$. A compound 2-2 was obtained using column chromatography.

500 MHz $^1$H-NMR ($CDCl_3$) δ (ppm): 0.89 (t, 3H), 1.07 (m, 2H), 1.18 (m, 2H), 1.27 (t, 3H), 1.32 (m, 2H), 1.49 (m, 1H), 1.88 (m, 2H), 1.95 (m, 1H), 2.16 (m, 1H), 2.26 (m, 1H), 3.73 (m, 1H), 4.12 (q, 2H), 5.60 (s, 1H).

(Step 2)

To a solution of 25.36 g of the compound 2-2 dissolved in MeOH, 1.28 g of 10% Pd/C was added, and the solution was reacted for 20 hours while maintaining the reaction flask under hydrogen atmosphere using a vacuum pump and hydrogen balloon. After the reaction was completed, Pd/C was filtered to remove, and the reaction solution was concentrated. A compound 2-3 was obtained using column chromatography.

500 MHz $^1$H-NMR ($CDCl_3$) δ (ppm): 0.87 (t, 3H), 0.94 (m, 3H), 1.15 (m, 2H), 1.25 (t, 3H), 1.30 (m, 3H), 1.48 (m, 1H), 1.69~1.75 (m, 5H), 2.16 (d, 2H), 4.12 (q, 2H).

(Steps 3~12)

A compound I-4a was synthesized by the methods similar to (Step 4)~(Step 13) of Example 1.

500 MHz $^1$H-NMR ($CDCl_3$) δ (ppm): 0.82~0.91 (m, 5H), 1.03 (m, 2H), 1.15~1.50 (m, 7H), 1.69 (m, 1H), 1.74~2.01 (m, 4H), 2.22 (m, 1H), 3.72 (m, 1H), 4.34 (m, 1H), 5.12 (m, 1H), 7.16 (m, 2H).

Example 5

Synthesis of Liquid Crystal Compounds of Formula I-54a

Reaction Scheme 5

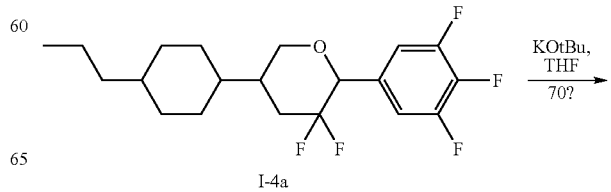

-continued

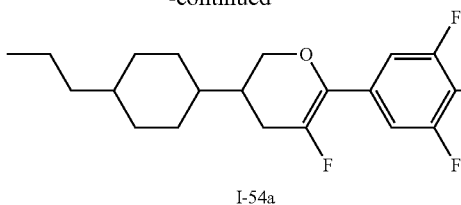

I-54a

A compound I-54a was obtained from the compound I-4a by the same method as Example 2.

500 MHz $^1$H-NMR (CDCl$_3$) δ (ppm): 0.84~0.90 (m, 5H), 1.01 (m, 2H), 1.16~1.53 (m, 7H), 1.71 (m, 1H), 1.73~1.98 (m, 4H), 2.18 (m, 1H), 3.65 (m, 1H), 4.29 (m, 1H), 7.17 (m, 2H).

Example 6

Synthesis of Liquid Crystal Compounds of Formula I-12a

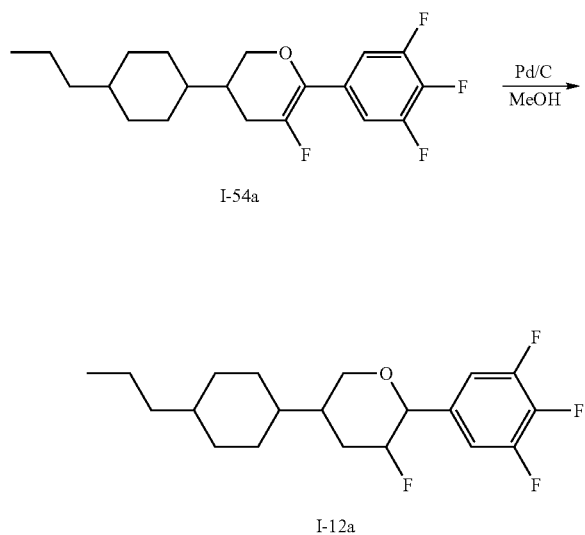

A compound I-12a was obtained from the compound I-54a by the same method as Example 3.

500 MHz $^1$H-NMR (CDCl$_3$) δ (ppm): 0.81~0.93 (m, 5H), 1.02 (m, 2H), 1.13~1.48 (m, 7H), 1.68 (m, 1H), 1.72~2.00 (m, 4H), 2.12 (m, 1H), 2.26 (m, 1H), 3.74 (m, 1H), 4.35 (m, 1H), 5.15 (m, 1H), 7.15 (m, 2H).

Examples 7

Examples of Representative Liquid Crystal Compositions

Two or more kinds of pyran derivatives of the Chemical Formula I were mixed to prepare liquid crystal compositions 1 to 7. Pyran derivatives comprised in the liquid compositions are represented by abbreviations as described in the following Table 1.

TABLE 1

| Ring structure | Symbol | Left end group | Symbol |
|---|---|---|---|
| | C | $C_nH_{2n+1}$— | n |
| | P | $C_nH_{2n+1}$CH=CH— | nV |
| | P(F) | $CH_2$=CH$C_nH_{2n}$— | Vn |
| | P(F,F) | Right end group | Symbol |
| | Pr | —O$C_nH_{2n+1}$ | —On |
| | Pr(F) | —F | —F |
| | Pr(2F) | —OCF$_3$ | —OCF3 |

In the above Table 1, n is represented by natural number.

For the liquid crystal compositions 1 to 7 comprising two or more kinds of pyran derivative of the Chemical Formula I (the contents of pyran derivatives comprised in the liquid crystal composition are as described below), physical properties were evaluated by the following methods.

For each liquid crystal composition, nematic liquid crystal transition temperature (Tni), refractive anisotropy (Δn) and dielectric anisotropy (Δ∈) were measured. First, a liquid crystal cell was manufactured to measure dielectric anisotropy (Δ∈) of the liquid crystal composition at 25° C. and 0.1 Hz, using Toyo Co. model 6254, and refractive anisotropy (Δn) using Abbe refractometer. And, nematic liquid crystal transition temperature (Tni) was measured using DSC.

| (Liquid crystal composition 1) | |
|---|---|
| Compound | content (wt %) |
| 3-PPr(F)P(F,F)-F | 13 |
| 4-PPr(F)P(F,F)-F | 13 |
| 3-PPr(2F)P(F,F)-F | 13 |
| 5-CP-F | 12 |

(Liquid crystal composition 1)

| Compound | content (wt %) |
|---|---|
| 6-CP-F | 9 |
| 7-CP-F | 5 |
| 2-CCP-OCF3 | 5 |
| 3-CCP-OCF3 | 5 |
| 4-CCP-OCF3 | 5 |
| 3-CCP(F,F)-OCF3 | 4 |
| 3-CPP(F)-F | 5 |
| 5-CPPC-3 | 5 |
| 3-CP(F)PC-3 | 3 |

Tni = 84.4;
Δn = 0.139;
Δε = 27.6

(liquid crystal composition 2)

| Compound | content (wt %) |
|---|---|
| 3-PPr(F)P(F,F)-F | 23 |
| 3-PPr(2F)P(F,F)-F | 23 |
| 3-CC-4 | 8 |
| 3-CCP-1 | 6 |
| 3-CCP(F,F)-F | 6 |
| 3-CPP(F,F)-F | 13 |
| 5-CPP(F,F)-F | 10 |
| 3-CCPP(F,F)-F | 8 |
| 3-CP(F)PC-3 | 3 |

Tni = 87.6;
Δn = 0.119;
Δε = 12.5

(liquid crystal composition 3)

| Compound | content (wt %) |
|---|---|
| 3-CPr(2F)P(F,F)-F | 13 |
| 4-CPr(2F)P(F,F)-F | 13 |
| 3-CPr(F)P(F,F)-F | 13 |
| V-CC-3 | 22 |
| 3-CCP(F,F)-F | 8 |
| 3-PP(F)P(F,F)-F | 7 |
| V-CCP-3 | 7 |
| V-CCP-1 | 7 |
| 5-CPPC-3 | 5 |
| 3-CP(F)PC-3 | 5 |

Tni = 100.3;
Δn = 0.107;
Δε = 10.8

(liquid crystal composition 4)

| Compound | content (wt %) |
|---|---|
| 3-Pr(F)P(F)P(F,F)-F | 6 |
| 4-Pr(F)P(F)P(F,F)-F | 6 |
| 3-Pr(F)P(F,F)P(F,F)-F | 5 |
| 3-Pr(F)PP(F,F)-F | 7 |
| 3-CPr(2F)P(F,F)-F | 10 |
| 4-CPr(2F)P(F,F)-F | 10 |
| 5-CPr(2F)P(F,F)-F | 10 |
| 5-CP-F | 12 |
| 6-CP-F | 9 |
| 7-CP-F | 5 |
| 3-CCP(F,F)-OCF3 | 4 |

(liquid crystal composition 4)

| Compound | content (wt %) |
|---|---|
| 3-CPP(F)-F | 5 |
| 5-CCP(F)-F | 5 |
| 5-CPPC-3 | 3 |
| 3-CP(F)PC-3 | 3 |

Tni = 87.5;
Δn = 0.112;
Δε = 8.9

(liquid crystal composition 5)

| Compound | content (wt %) |
|---|---|
| 3-CPr(2F)P(F,F)-F | 11 |
| 4-CPr(2F)P(F,F)-F | 11 |
| 3-Pr(2F)P(F)P(F,F)-F | 5 |
| 3-Pr(2F)P(F,F)P(F,F)-F | 5 |
| 5-CP-F | 6 |
| 6-CP-F | 6 |
| 7-CP-F | 5 |
| V-CCP-1 | 8 |
| V-CCP-3 | 9 |
| 3-CC-3 | 8 |
| 3-CC-4 | 8 |
| 3-PP(F)P(F,F)-F | 7 |
| 5-CCP(F)-F | 5 |
| 5-CPPC-3 | 3 |
| 3-CP(F)PC-3 | 3 |

Tni = 86.2;
Δn = 0.123;
Δε = 13.2

(liquid crystal composition 6)

| Compound | content (wt %) |
|---|---|
| 3-CPr(F)P(F,F)-F | 10 |
| 4-CPr(F)P(F,F)-F | 10 |
| 3-CPrP(F,F)-F | 6 |
| 2-CP-F | 5 |
| 3-CP-F | 10 |
| 3-CP-O2 | 14 |
| 3-CCP-F | 4 |
| 3-CCP-1 | 8 |
| 3-CCP-O1 | 5 |
| 3-CCP-3 | 10 |
| 2-CCP(F)-F | 4 |
| 3-CCP(F)-F | 4 |
| 5-CCP(F)-F | 5 |
| 3-CCP(F,F)-F | 5 |

Tni = 106.3;
Δn = 0.097;
Δε = 7.9

(liquid crystal composition 7)

| Compound | content (wt %) |
|---|---|
| 3-CPr(F)P(F,F)-F | 11 |
| 4-CPr(F)P(F,F)-F | 11 |
| 3-PPr(2F)P(F,F)-F | 11 |
| 3-Pr(2F)P(F)P(F,F)-F | 9 |
| 7-CP(F,F)-F | 3 |
| 3-CC-4 | 10 |

-continued (liquid crystal composition 7)

| Compound | content (wt %) |
| --- | --- |
| 3-CC-5 | 5 |
| 3-CP-O2 | 7 |
| 3-CCP-1 | 7 |
| 3-CCP-O1 | 5 |
| 2-CCP(F)-F | 4 |
| 3-CPP(F)-F | 5 |
| 5-CCP(F)-F | 4 |
| 3-CCP(F,F)-F | 5 |
| 3-CP(F)PC-3 | 3 |

Tni = 88.6;
Δn = 0.127;
Δε = 12.9

From the measurement results of nematic liquid crystal transition temperature (Tni), refractive anisotropy (Δn) and dielectric anisotropy (Δε), it is confirmed that the liquid crystal compositions 1 to 7 comprising two or more kinds of pyran derivatives of the Chemical Formula I manifest appropriate refractive anisotropy and liquid crystal transition temperature and relatively high positive dielectric anisotropy, and thus it can be preferably used for the formation of a liquid crystal layer of a liquid crystal display device.

Especially, the liquid crystal compositions have excellent compatibility with various liquid crystal compositions to show excellent physical properties, and thus, it is possible to suitably mix liquid crystal compounds to control physical properties of the composition, and therefore, the liquid crystal compositions can satisfy various physical properties required in various liquid crystal display devices and can be used for the formation of a liquid crystal layer of various liquid crystal display devices.

What is claimed is:

1. A pyran derivative of the following formula I:

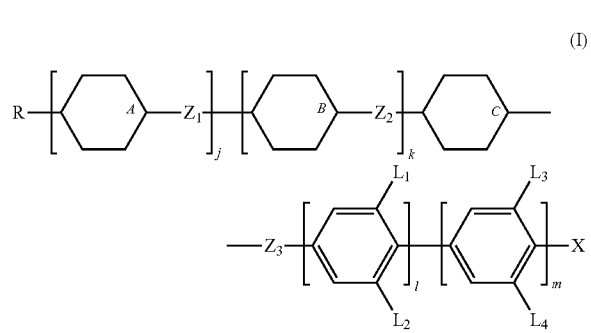

Wherein
R is H, $C_1$~$C_{15}$ alkyl, $C_2$~$C_{15}$ alkenyl or $R_1O$—; $R_1$ is H, $C_1$~$C_{15}$ alkyl or $C_2$~$C_{15}$ alkenyl group;
ring C is

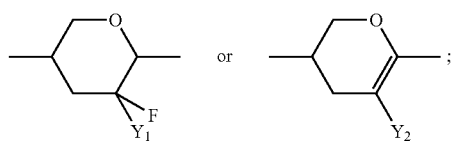

ring A and ring B are independently

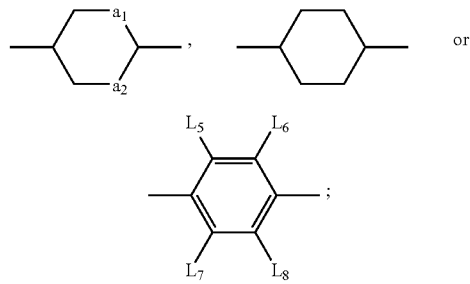

$Y_1$ is H, F, Cl, CN or $CF_3$; $Y_2$ is F, Cl, CN or $CF_3$; $a_1$ and $a_2$ are independently O or N;

$Z_1$, $Z_2$ and $Z_3$ are independently —$(CH_2)_n$— (n is 0 or 2), —C≡C—, —C(=O)O—, —OC(=O)—, —$CF_2$O—, —$OCF_2$—, —OC(=O)O—, —$CH_2$O—, —$CH_2$C(=O)—, —$OCH_2$— or —C(=O)$CH_2$—;

X is Cl, F, $CF_3$, $OCF_3$, $OCHF_2$, $CHF_2$, $CH_2F$, $OCF_2CHF_2$ or $OCF_2CHFCH_3$;

$L_1$ to $L_8$ are independently H or F; and, j, k, l, and m are independently 0, 1 or 2.

2. The pyran derivative according to claim 1, wherein the $C_2$~$C_{15}$ alkenyl group is —CH=$CH_2$, —CH=$CHCH_3$ (E,Z), —$CH_2$CH=$CH_2$, —CH=$CHCH_2CH_3$ (E,Z), —$CH_2$CH=$CHCH_3$ (E,Z), —$CH_2CH_2$CH=$CH_2$, —CH=$CHCH_2CH_2CH_3$ (E,Z), —$CH_2$CH=$CHCH_2CH_3$ (E,Z), —$CH_2CH_2$CH=$CHCH_3$ (E,Z) or —$CH_2CH_2CH_2$CH=$CH_2$.

3. The pyran derivative according to claim 1, wherein the ring A or the ring B is

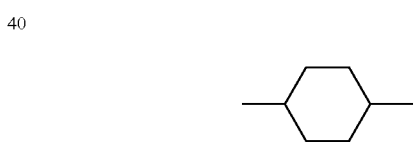

or the ring C is

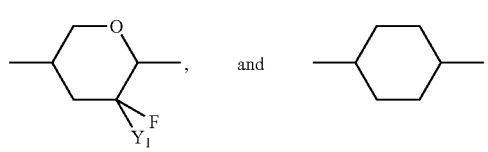

of the ring A or B or

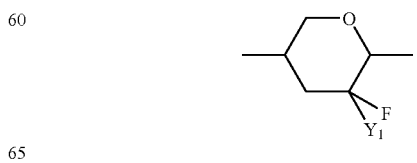

of the ring C is in the form of trans-stereoisomer.

4. The pyran derivative according to claim 1, wherein the ring C is
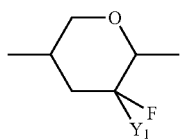
(provided that $Y_1$ is not fluorine), and fluorine of the ring C is bonded in an equatorial position.
5. The pyran derivative according to claim 1, wherein the pyran derivative is selected from the group consisting of compounds having the following formulae I-1 to I-70:
I-1
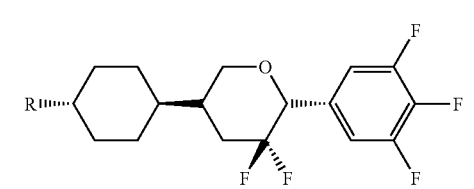
I-2
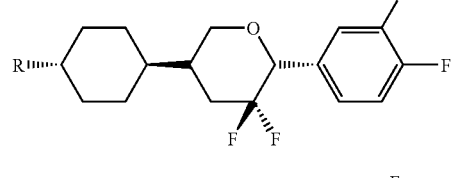
I-3
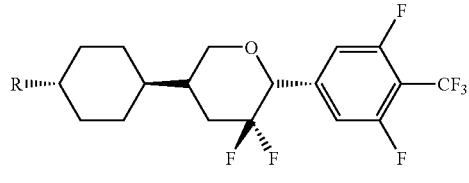
I-4
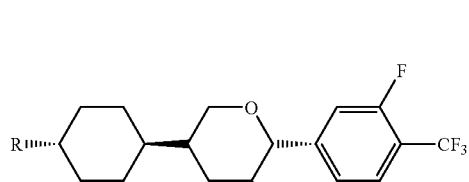
I-5
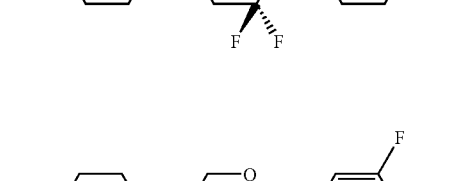
I-6
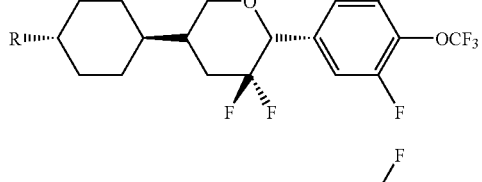
-continued
I-7
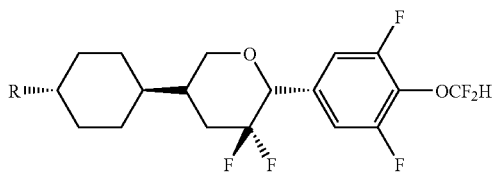
I-8
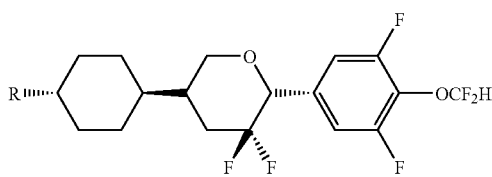
I-9
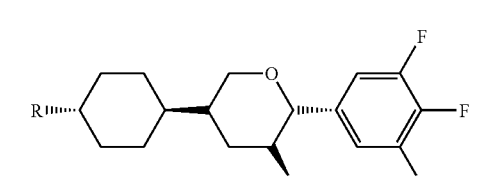
I-10
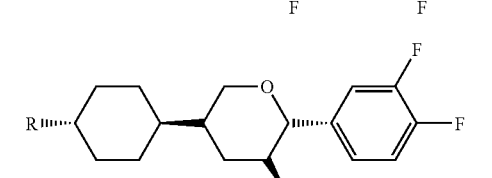
I-11
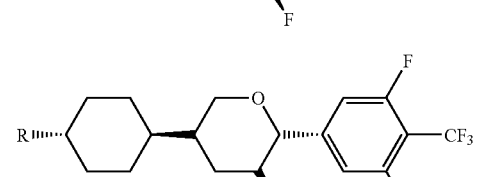
I-12
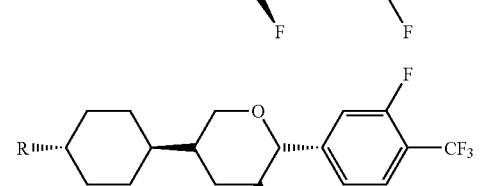
I-13
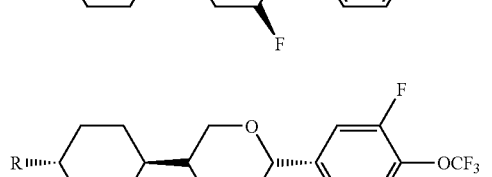
I-14
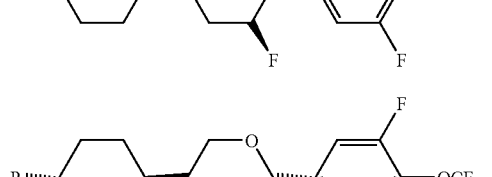
I-15
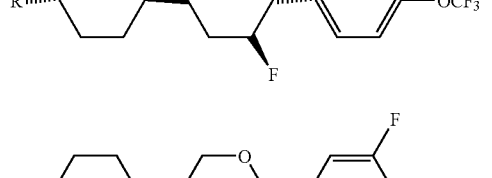

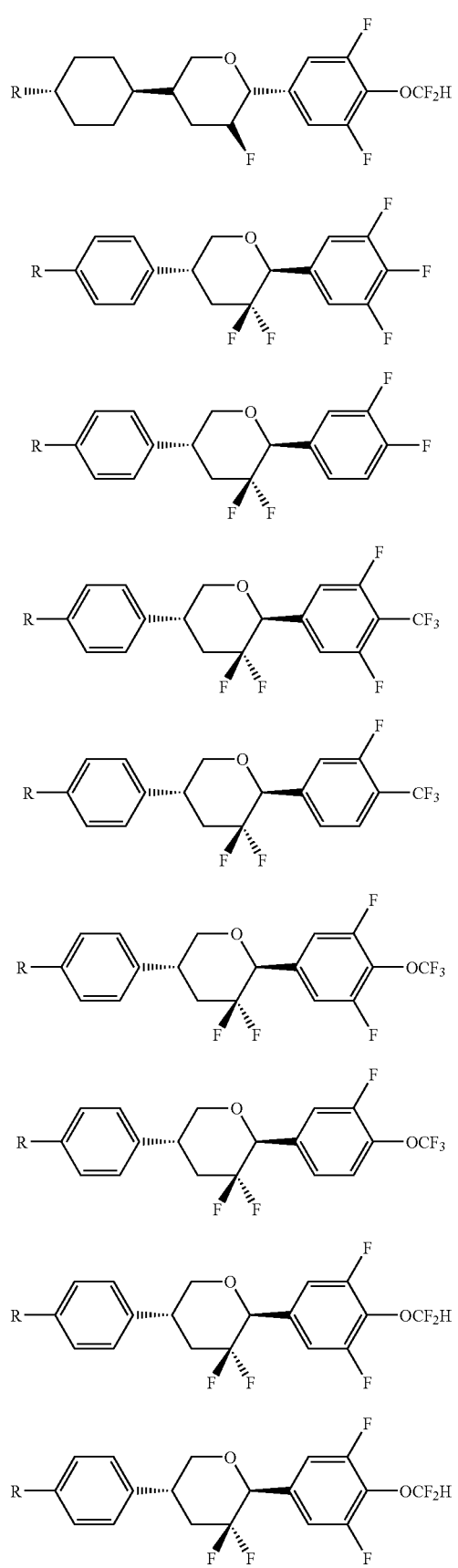

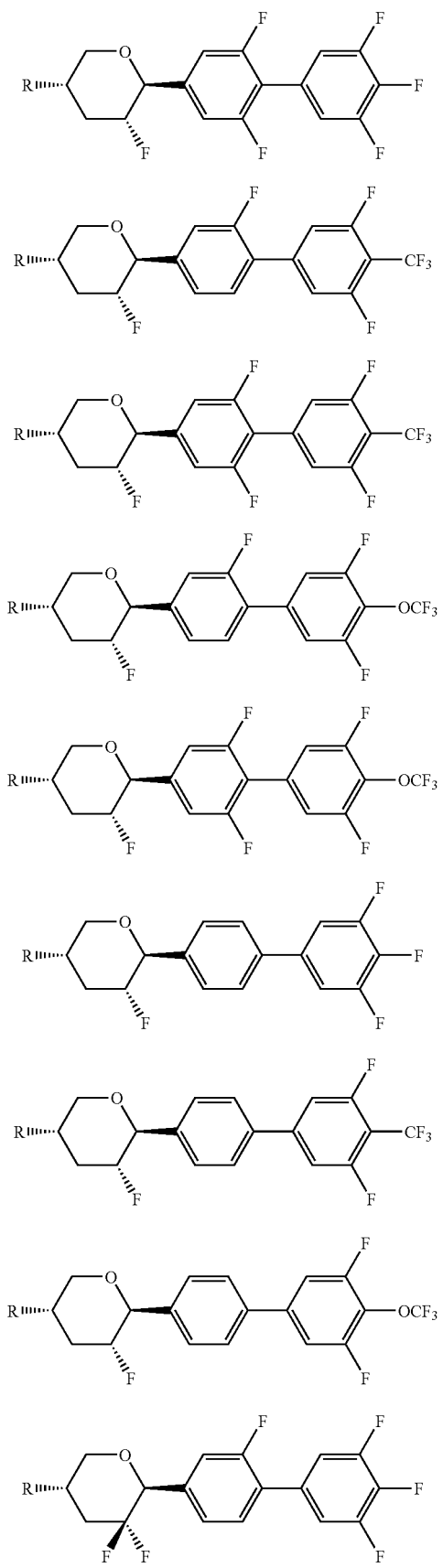
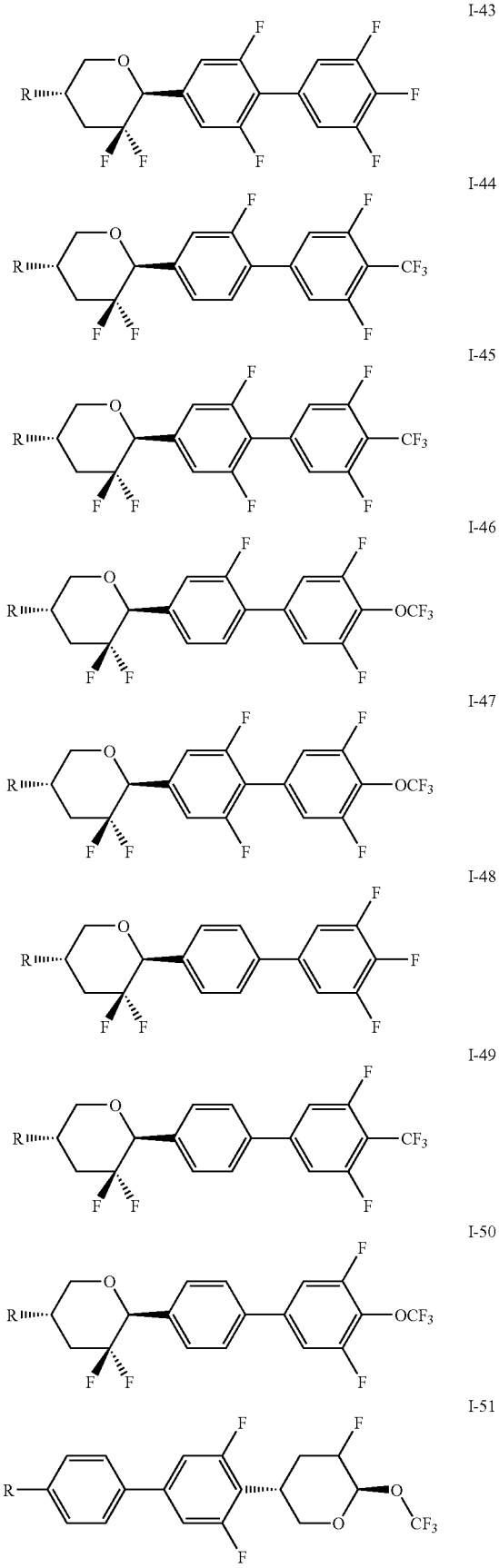

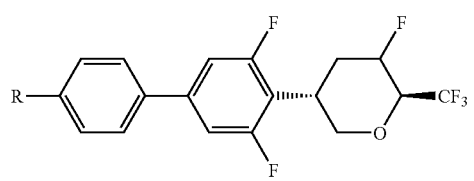 I-52
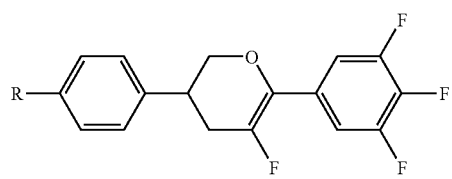 I-53
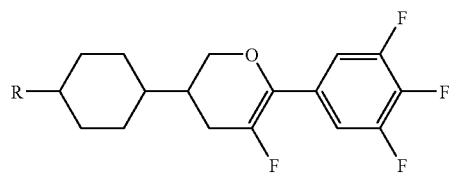 I-54
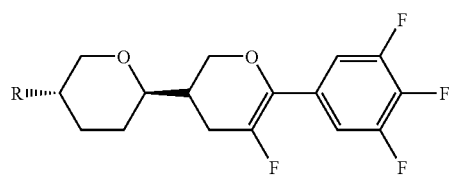 I-55
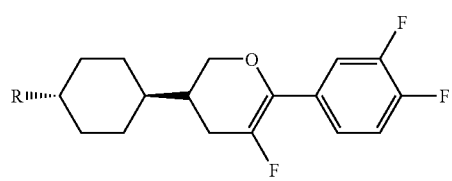 I-56
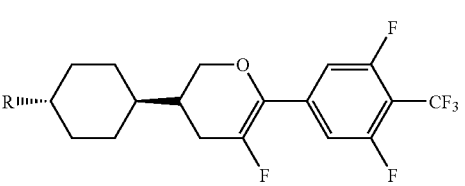 I-57
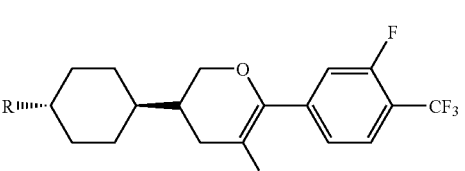 I-58
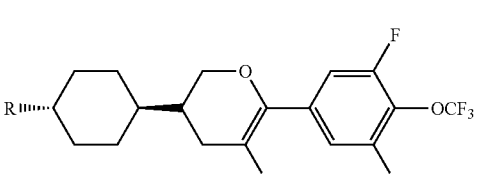 I-59
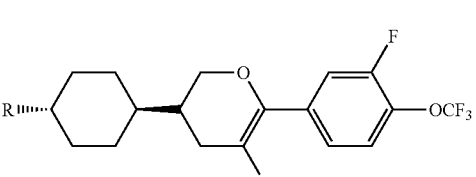 I-60
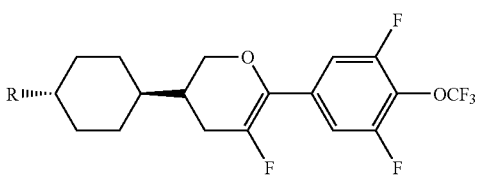 I-61
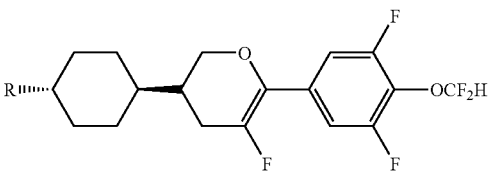 I-62
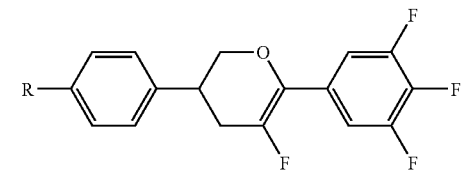 I-63
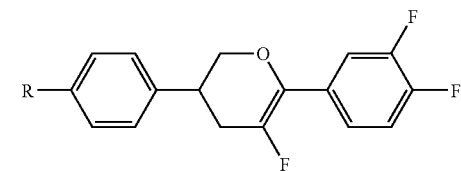 I-64
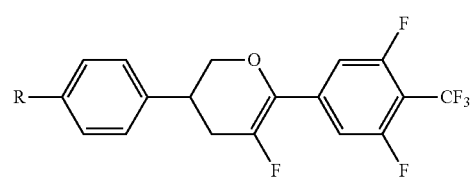 I-65
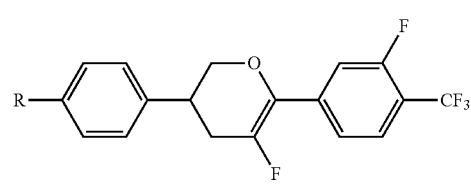 I-66
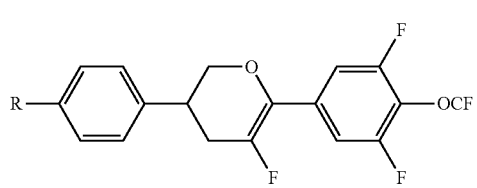 I-67
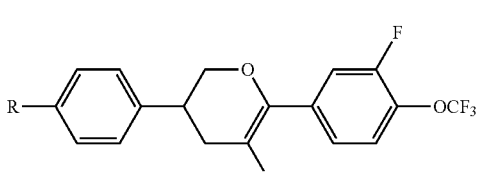 I-68
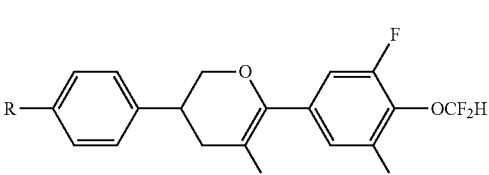 I-69

-continued

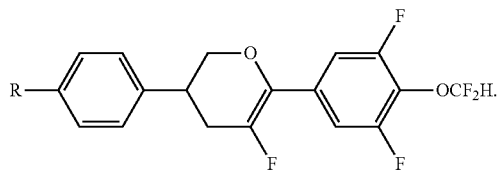

I-70

6. The pyran derivative according to claim 1, wherein the pyran derivative is used for a liquid crystal compound for a liquid crystal layer of a liquid crystal display device.

7. A method for preparing a pyran derivative comprising the steps of:

cyclizing a compound of the following Chemical Formula II to form a compound of the following Chemical Formula III; and forming a pyran derivative of the following Chemical Formula I from the compound of the Chemical Formula III:

wherein,

R is H, $C_1 \sim C_{15}$ alkyl, $C_2 \sim C_{15}$ alkenyl group or $R_1O-$; $R_1$ is H, $C_1 \sim C_{15}$ alkyl or $C_2 \sim C_{15}$ alkenyl group;

ring C is

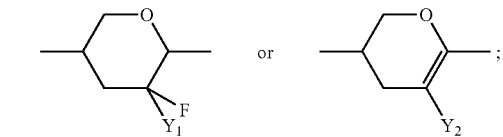

ring A and ring B are independently

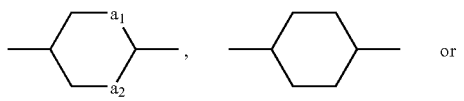

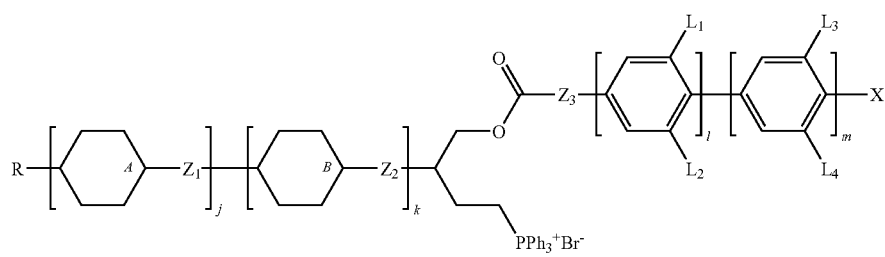

(II)

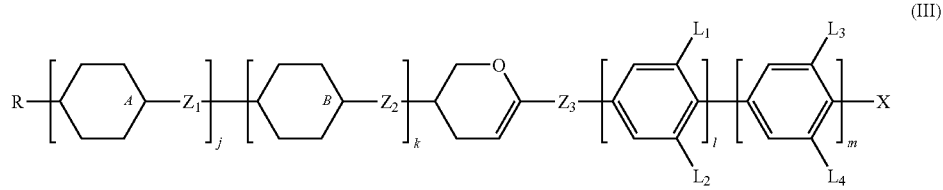

(III)

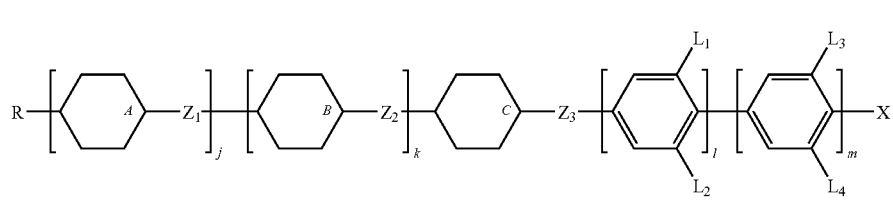

(I)

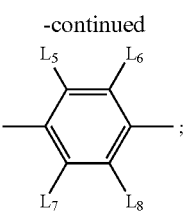

$Y_1$ is H, F, Cl, CN or $CF_3$; $Y_2$ is F, Cl, CN or $CF_3$; $a_1$ and $a_2$ are independently O or N;

$Z_1$, $Z_2$ and $Z_3$ are independently —$(CH_2)_n$— (n is 0 or 2), —C≡C—, —C(=O)O—, —OC(=O)—, —$CF_2$O—, —$OCF_2$—, —OC(=O)O—, —$CH_2$O—, —$CH_2$C(=O)—, —$OCH_2$— or —C(=O)$CH_2$—;

X is Cl, F, $CF_3$, $OCF_3$, $OCHF_2$, $CHF_2$, $CH_2F$, $OCF_2CHF_2$ or $OCF_2CHFCH_3$;

$L_1$ to $L_8$ are independently H or F; and, j, k, l and m are 0, 1 or 2.

8. The method according to claim 7, wherein the step of forming the pyran derivative comprises fluorinating the compound of the Chemical Formula III to form a compound of the following Chemical Formula IV:

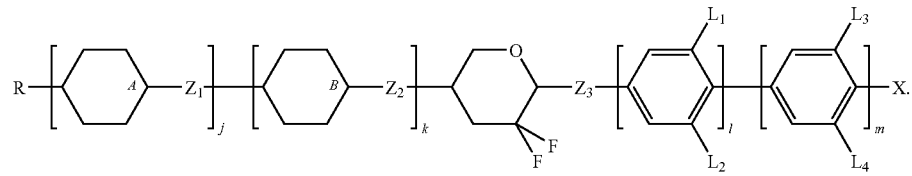

9. The method according to claim 8, further comprising the step of defluorinating the compound of the Chemical Formula IV to form a compound of the following Chemical Formula V:

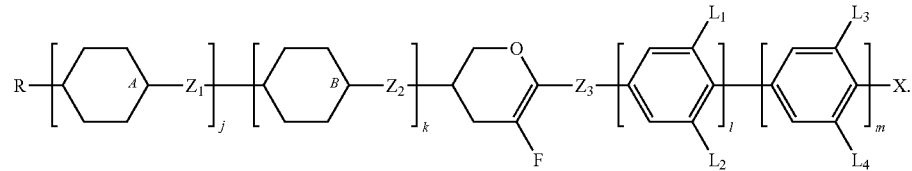

10. The method according to claim 9, further comprising the step of hydrogenating the compound of the Chemical Formula V to form a compound of the following Chemical Formula VI:

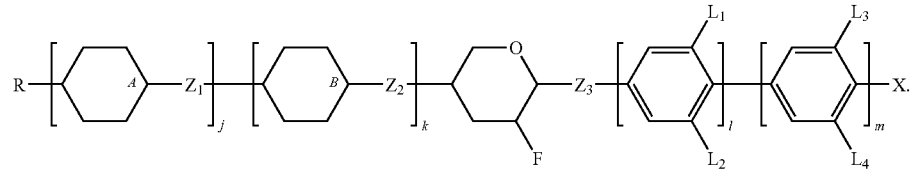

11. A liquid crystal composition comprising one or more kinds of the pyran derivatives of claim 1.

12. The liquid crystal composition according to claim 11, wherein the composition comprises 1 to 50 wt % of each of the pyran derivatives, based on the total weight of the liquid crystal composition.

13. The liquid crystal composition according to claim 11, wherein the composition comprises one or more kinds of pyran derivatives wherein the ring A or the ring B is

or the ring C is

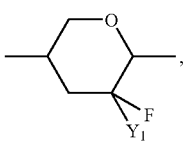

and the pyran derivatives comprise a compound wherein

of the ring A or B or

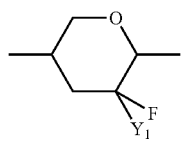

of the ring C is in the form of trans-stereoisomer and a compound wherein

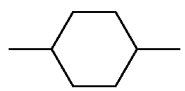

of the ring A or B or

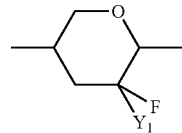

of the ring C is in the form of cis-stereoisomer in a mole ratio of 85:15.

14. The liquid crystal composition according to claim 11, wherein the composition comprises one or more kinds of pyran derivatives wherein the ring C is

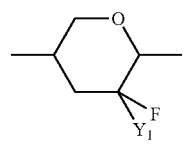

(provided that $Y_1$ is not fluorine), and the fluorine of the ring C is bonded in an equatorial position.

15. A liquid crystal display device which comprises a liquid crystal layer comprising the liquid crystal composition of claim 11.

16. The liquid crystal display device according to claim 15, wherein the liquid crystal display device is simple matrix type twisted nematic liquid crystal display, simple matrix type supertwisted nematic liquid crystal display, active TFT liquid crystal display, active MIM liquid crystal display or active IPS liquid crystal display.

17. The pyran derivative according to claim 2, wherein the pyran derivative is used for a liquid crystal compound for a liquid crystal layer of a liquid crystal display device.

18. The pyran derivative according to claim 3, wherein the pyran derivative is used for a liquid crystal compound for a liquid crystal layer of a liquid crystal display device.

19. The pyran derivative according to claim 4, wherein the pyran derivative is used for a liquid crystal compound for a liquid crystal layer of a liquid crystal display device.

20. The pyran derivative according to claim 5, wherein the pyran derivative is used for a liquid crystal compound for a liquid crystal layer of a liquid crystal display device.

* * * * *